(12) United States Patent
Weiss et al.

(10) Patent No.: US 8,021,384 B2
(45) Date of Patent: Sep. 20, 2011

(54) EXTENDING INTRABODY CAPSULE

(76) Inventors: Ram Weiss, Haifa (IL); Menachem P. Weiss, Haifa (IL)

(*) Notice: Subject to any disclaimer, the term of this patent is extended or adjusted under 35 U.S.C. 154(b) by 774 days.

(21) Appl. No.: 11/627,189

(22) Filed: Jan. 25, 2007

(65) Prior Publication Data

US 2007/0123809 A1  May 31, 2007

Related U.S. Application Data

(63) Continuation-in-part of application No. PCT/IL2006/000845, filed on Jul. 20, 2006.

(60) Provisional application No. 60/702,782, filed on Jul. 26, 2005.

(51) Int. Cl.
*A61M 29/00* (2006.01)

(52) U.S. Cl. ...................... 606/191; 623/23.65

(58) Field of Classification Search .......... 604/104–106; 623/23.64–23.66, 23.75, 24; 606/191
See application file for complete search history.

(56) References Cited

U.S. PATENT DOCUMENTS

| | | | |
|---|---|---|---|
| 3,719,183 A | 3/1973 | Schwartz | |
| 4,246,893 A | 1/1981 | Berson | |
| 4,315,509 A | 2/1982 | Smit | |
| 4,416,267 A | 11/1983 | Garren et al. | |
| 4,485,805 A | 12/1984 | Foster, Jr. | |
| 4,607,618 A | 8/1986 | Angelchik | |
| 4,648,383 A | 3/1987 | Angelchik | |
| 5,002,772 A * | 3/1991 | Curatolo et al. | 424/438 |
| 5,443,843 A | 8/1995 | Curatolo et al. | |
| 5,609,606 A | 3/1997 | O Boyle | |
| 5,733,313 A | 3/1998 | Barreras, Sr. et al. | |
| 5,868,141 A | 2/1999 | Ellias | |
| 5,984,860 A | 11/1999 | Shan | |
| 5,993,473 A | 11/1999 | Chan et al. | |
| 6,454,785 B2 | 9/2002 | De Hoyos Garza et al. | |
| 6,719,684 B2 | 4/2004 | Kim et al. | |
| 6,733,512 B2 | 5/2004 | McGhan | |
| 6,783,499 B2 | 8/2004 | Schwartz et al. | |
| 6,911,004 B2 | 6/2005 | Kim et al. | |
| 2001/0051766 A1 | 12/2001 | Gazdzinski | |
| 2002/0183783 A1 | 12/2002 | Shadduck | |
| 2003/0078611 A1 | 4/2003 | Hashiba et al. | |
| 2003/0216622 A1 * | 11/2003 | Meron et al. | 600/300 |
| 2004/0122453 A1 | 6/2004 | Deem et al. | |
| 2004/0181155 A1 | 9/2004 | Glukhovsky | |

(Continued)

FOREIGN PATENT DOCUMENTS

WO  WO-2006035446  4/2006

(Continued)

OTHER PUBLICATIONS

U.S. Appl. No. 60/702,782, filed Jul. 26, 2005.

(Continued)

*Primary Examiner* — Ryan Severson
(74) *Attorney, Agent, or Firm* — Fish & Richardson P.C.

(57) ABSTRACT

A medical device includes a device body for insertion into an organ of a patient and one or more arms, which are attached to the device body and are arranged to extend outward from the device body within the organ so as to contact respective points-of-contact on an inner surface of the organ, and to apply a repetitive motion at one or more of the points-of-contact.

108 Claims, 12 Drawing Sheets

U.S. PATENT DOCUMENTS

| | | |
|---|---|---|
| 2004/0186503 A1 | 9/2004 | DeLegge |
| 2005/0033202 A1 | 2/2005 | Chow et al. |
| 2005/0183732 A1 | 8/2005 | Edwards |
| 2005/0245957 A1 | 11/2005 | Starkebaum et al. |
| 2006/0155311 A1 | 7/2006 | Hashiba et al. |
| 2006/0276729 A1 | 12/2006 | Reed et al. |

FOREIGN PATENT DOCUMENTS

| | | |
|---|---|---|
| WO | WO-2006035467 | 4/2006 |
| WO | WO-2006092789 | 9/2006 |
| WO | WO-2007013059 | 2/2007 |
| WO | WO-2007136735 | 11/2007 |

OTHER PUBLICATIONS

An Office Action dated Dec. 9, 2010, which issued during the prosecution of Applicant's Chinese Patent Application No. 200680031191.1.

* cited by examiner

Fig. 5a
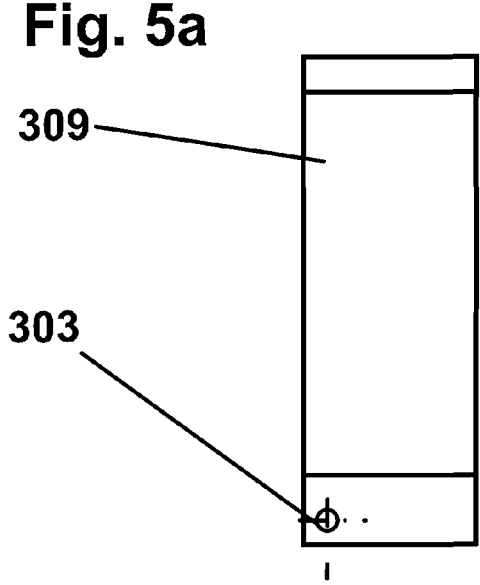
309
303
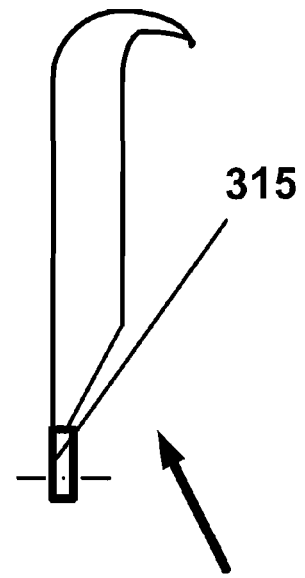
315
FIG. 5b
301
FIG. 5c
FIG. 5d    FIG. 5e
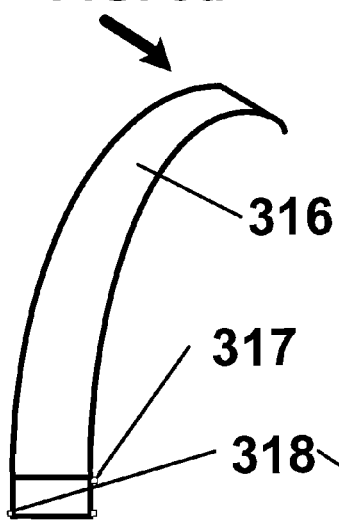
316
317
318

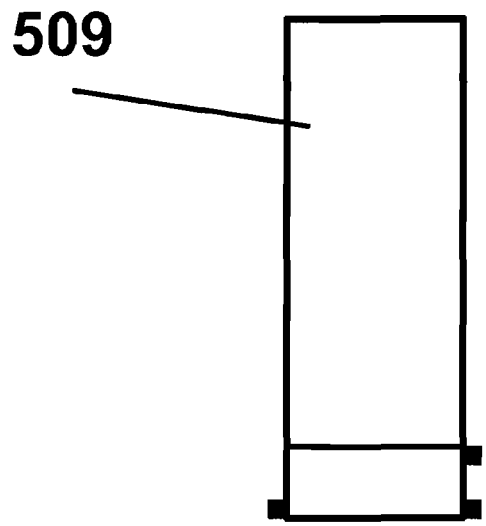
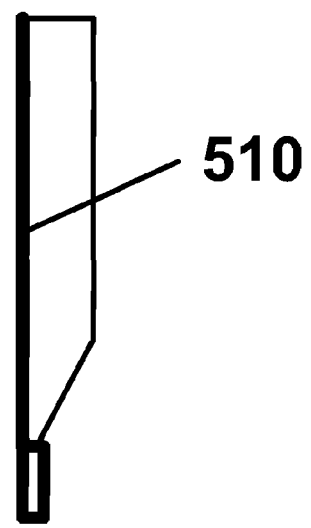
FIG. 7a  FIG. 7b
FIG. 7c 701
703
704
706 702 705

717
711
713
715
714 716

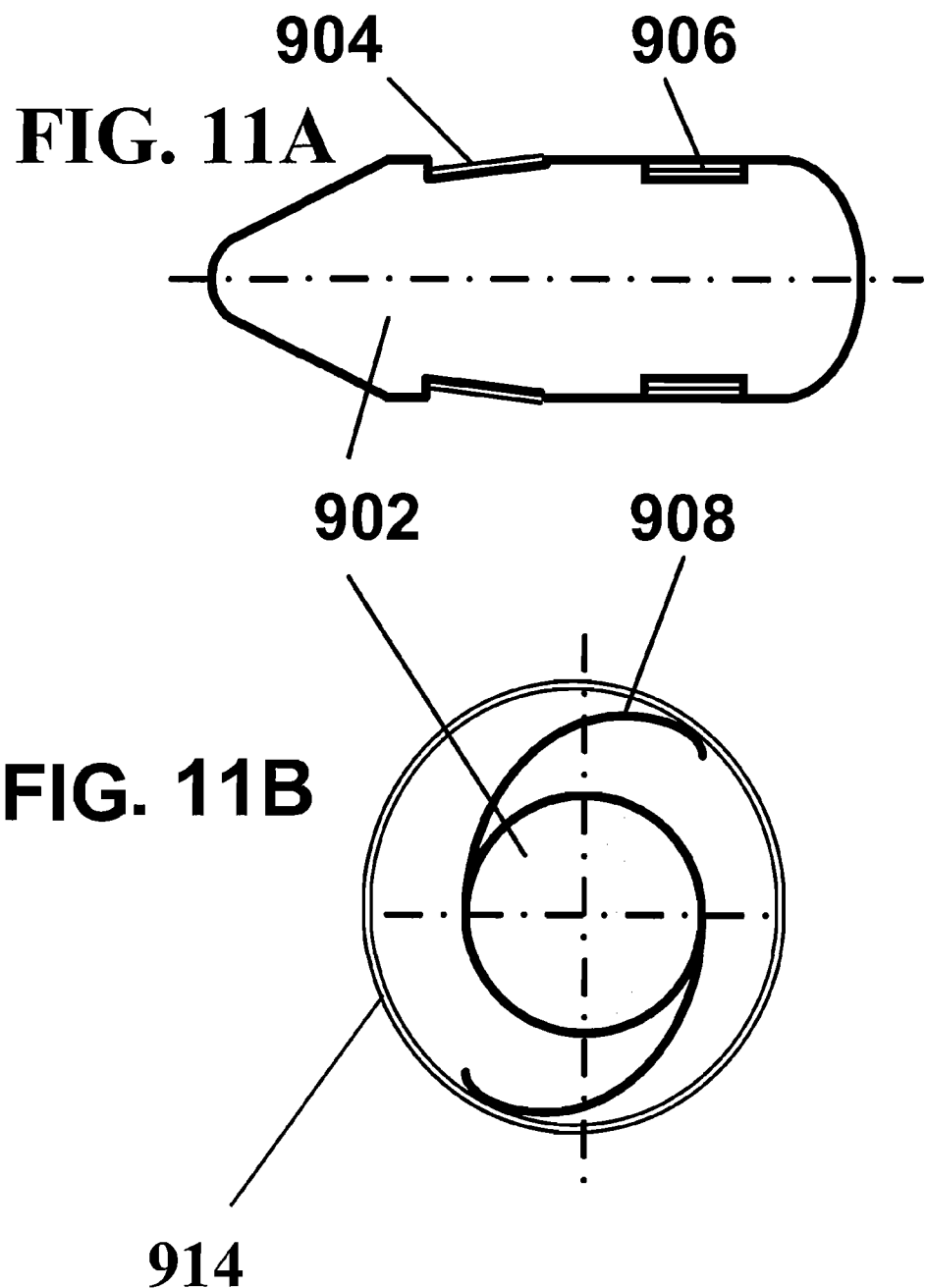

EXTENDING INTRABODY CAPSULE

CROSS-REFERENCE TO RELATED APPLICATIONS

This application is a continuation in part of PCT Patent Application PCT/IL2006/000845, filed Jul. 20, 2006, which claims the benefit of U.S. Provisional Patent Application 60/702,782, filed Jul. 26, 2005. Both of these parent applications are incorporated herein by reference.

FIELD OF THE INVENTION

The present invention relates generally to medical devices, and particularly to intrabody capsules.

BACKGROUND OF THE INVENTION

Various devices for insertion into the body for diagnostic, therapeutic and/or sensing purposes are known in the art. For example, U.S. Patent Application Publication 2003/0216622, whose disclosure is incorporated herein by reference, describes an in-vivo device capable of passing through a body lumen and whose geometry can alter or be altered. The device may include a device body and at least one appendage coupled to the body. The appendage(s) may be extended in vivo, thereby altering the device geometry while in a body lumen. The device may be a sensing device, a diagnostic device, a therapeutic device, or a combination thereof.

U.S. Patent Application Publication 2004/0181155, whose disclosure is incorporated herein by reference, describes an in vivo device for sensing a lumen such as the gastrointestinal (GI) tract. The device includes a substantially spherical housing and an oblong appendage attached to the housing. The appendage may be detached in vivo, for example in the stomach. The in vivo device may then roll and glide along a stomach wall to provide, for example, a smooth sampled image stream.

U.S. Pat. No. 5,984,860, whose disclosure is incorporated herein by reference, describes a pass-through duodenal enteroscopic device, which utilizes the natural contraction wave of the small intestine to propel the device through the small intestine. The exterior of the device is streamlined over the greater portion thereof with a video camera and illumination source at the forward end of the device. A transparent inflatable balloon covers the camera lens and illumination source, and is adapted to gently expand the small intestine immediately forward the camera for better viewing.

U.S. Pat. No. 6,719,684, whose disclosure is incorporated herein by reference, describes a micro-capsule robot for examining the internal organs of a human body. The robot can be fixed at a certain position in the body or its movement can be delayed, according to an external stop control signal.

U.S. Patent Application Publication 2001/0051766, whose disclosure is incorporated herein by reference, describes an endoscopic device, which is introduced into the intestinal tract of a living organism and operates autonomously therein. The device is adapted to obtain and store or transmit one or more types of data, such as visual image data, laser autofluorescence data and ultrasonic waveform data.

U.S. Pat. No. 6,783,499, whose disclosure is incorporated herein by reference, describes an implantable medical device. First and second sets of anchoring members are respectively connected to the proximal and distal ends of the device housing. The first and second sets of anchoring members are movable between a collapsed position and a deployed position. Each anchoring member comprises a ring member, and each ring member has a tissue engaging surface thereon.

U.S. Pat. No. 3,719,183, whose disclosure is incorporated herein by reference, describes an electronic capsule transponder, which has an insulating coating of material dissolvable by the action of enzyme secretions. The capsule circuitry is inoperable because of a pair of open connectors. When the coating is dissolved, the transponder is coated with the enzyme flow. As digestion proceeds, the electrodes comprising the open circuit are in contact with pancreatic and intestinal fluid, which has sufficient ions to provide a conductive path to close the open circuit. The capsule condition can then be detected by the external sensing means.

Intrabody devices are sometimes used for treating obesity. For example, U.S. Pat. No. 4,607,618, whose disclosure is incorporated herein by reference, describes a method for treatment of morbid obesity. A hollow-shaped appliance is placed in a patient stomach. The appliance is formed of semi-rigid skeleton members and is collapsible to a dimension and shape which can be inserted into the stomach through the esophagus and cardiac opening. Upon release of the collapsed device in the stomach, it autogeneously re-assumes its normal uncollapsed shape.

U.S. Pat. No. 4,648,383, whose disclosure is incorporated herein by reference, describes an apparatus for treatment of morbid obesity. The apparatus includes a collapsible intragastric appliance, which can be temporarily deformed to pass through the esophagus and cardiac opening of the stomach and to autogeneously assume a normal shape after it is received in the stomach to stimulate neuro-receptors in the sub-mucosa of the gastric fundus. Means are provided for detachably connecting the appliance to the lower end of an elongate, semi-rigid inserter rod which is passed through an aperture formed in the appliance to effect the detachable connection. Downward pressure on the inserter rod forces the collapsed appliance through the esophagus and cardiac opening into the stomach and slight upward force of the inserter rod is thereafter applied to detach the rod from the appliance.

PCT Patent Application Publication WO 2006/035446, whose disclosure is incorporated herein by reference, describes an apparatus and a method for treating a weight disorder in a subject. The apparatus comprises an implantable device, such as an inflatable balloon, electrodes capable of sensing a physiological change associated with good ingestion or hunger, and a mechanism adapted for directly stimulating a region, which is responsive to a gastrointestinal satiety agent. Such a mechanism can be a drug reservoir containing a drug such as CCK or analogs thereof, which is contained within an inflatable balloon in a stomach of the subject.

Other methods for treating obesity involve the insertion of an elastic expandable device, such as an inflatable balloon, into the patient's stomach. Such methods are described, for example, in U.S. Pat. Nos. 5,993,473, 6,454,785, 4,246,893, 4,485,805, 4,315,509, 4,416,267 and 6,733,512, whose disclosures are incorporated herein by reference.

Other disclosed methods treat obesity by applying electric signals and currents to the stomach. Such methods are described, for example, in U.S. Patent Application Publications 2004/0122453, 2005/0245957 and 2005/0183732 whose disclosures are incorporated herein by reference.

SUMMARY OF THE INVENTION

There is therefore provided, in accordance with an embodiment of the present invention, a medical device, including:
a device body for insertion into an organ of a patient; and
one or more arms, which are attached to the device body and are arranged to extend outward from the device body within the organ so as to contact respective points-of-contact on an inner surface of the organ, and to apply a repetitive motion at one or more of the points-of-contact.

In some embodiments, the repetitive motion includes at least one motion type selected from a group of types consisting of a sliding motion, a tilting motion and a perpendicular pressure motion. In a disclosed embodiment, the arms are arranged, when extended, to apply at least one stimulation type selected from a group of types consisting of a mechanical, a vibratory, a tactile and a nociceptive stimulation at the respective points-of-contact on the inner surface of the organ.

In an embodiment, the organ includes a stomach of the patient. In another embodiment, the organ includes one of a gastrointestinal tract of the patient, a blood vessel, a genitourinary tract of the patient, part of a central nervous system, an intra-abdominal organ, a thoracic organ and a limb of the patient. In yet another embodiment, the device includes a capsule that is arranged to be swallowed by the patient. Alternatively, the device may be arranged to be inserted into the organ using at least one procedure selected from a group of procedures consisting of an invasive procedure, an endoscopic procedure, a laparoscopic surgery procedure and a surgical laparotomy procedure.

In some embodiments, the arms include at least one of a metal, a plastic, an electrically-actuated material, an ionic Electro-Active Polymer (EAP), an electronic EAP, a Dielectric Elastomer Actuator (DAE) and a piezoelectric material. In an embodiment, the arms have distal ends, and the repetitive motion measured at the distal ends of the arms has a frequency between 0.1 Hz and 50 Hz and an amplitude of between 10 microns and 100 mm.

In another embodiment, the device includes an antenna and a receiver, which are arranged to receive external commands transmitted to the device from an external transmitter, and a controller, which is arranged to control an operation of the device responsively to the external commands. The controller may be arranged to cause the arms to extend from the device body responsively to the external commands. Additionally or alternatively, the controller may be arranged to cause the arms to disengage from the device body responsively to the external commands.

In yet another embodiment, the arms have respective bases and include at least one releasable attachment mechanism for attaching the bases to the device body when the arms are extended, the attachment mechanism selected from a group of mechanisms consisting of a friction mechanism, a pin mechanism and a taper mechanism.

In still another embodiment, the device includes a release mechanism, which is arranged to restrain the arms during the insertion into the organ, and a controller, which is arranged to actuate the release mechanism to release the arms, so as to permit extension of the arms within the organ. In a disclosed embodiment, the arms are elastic and arranged to assume an extended position when not restrained, and are wrapped around the device body during the insertion into the organ. The arms may be wrapped around the device body in multiple layers.

In an embodiment, the arms include at least one material selected from a group of materials consisting of a piezoelectric material, a Dielectric Elastomer Actuator (DEA), an ionic Electro-Active Polymer (EAP) and an electronic EAP, and the controller is arranged to apply a voltage to the material so as to cause the arms to extend.

In another embodiment, the controller is arranged to determine a release condition and to actuate the release mechanism responsively to the release condition so as to cause the release mechanism to release the arms. The release condition may include at least one of a predetermined time schedule, an event schedule and an external command transmitted to the device. The release mechanism may include at least one actuation device selected from a group of mechanisms consisting of a shape memory alloy (SMA) element, a motor, a piezoelectric element, an Electro-Active Polymer (EAP) element, a Dielectric Elastomer Actuator (DEA), a solenoid, a magnetic lock and a detent, and the controller may be arranged to actuate the release mechanism using the actuation device.

In yet another embodiment, the device includes a cover including a dissolvable material, which is arranged to restrain the arms during the insertion into the organ and to dissolve in the organ so as to release the arms and permit the arms to extend. Dissolution of the cover can be actuated by consumption of a substance by the patient.

In still another embodiment, the device includes a disassembly mechanism, which is arranged, when activated, to disengage the arms from the device body so as to allow the device body and the arms to be disposed of. The disassembly mechanism may perform at least one action selected from a group of actions consisting of:

releasing a circumferential ring that holds a first side of a base of the arms;
moving outward parts that are adjacent to a second side of the base of the arms opposite the first side;
removing pivots connecting the arms to the device body;
releasing a friction mechanism; and
pushing the base of the arms out of a tapered locking mechanism.

In an embodiment, the disassembly mechanism includes one or more pre-energized springs that are released when the disassembly mechanism is activated. In another embodiment, the arms include respective pivots connecting the arms to the device body, and the disassembly mechanism is arranged to remove the pivots when activated.

In another embodiment, the device includes a controller, which is arranged to actuate the disassembly mechanism responsively to a disassembly condition. The disassembly condition may include at least one condition selected from a group of conditions consisting of a predetermined time schedule, a low power condition of a power source of the device and an external command transmitted to the device. In some embodiments, the disassembly mechanism includes at least one actuation element selected from a group of elements consisting of a shape memory alloy (SMA) element, a motor, a piezoelectric element, an Electro-Active Polymer (EAP) element, a solenoid, a ball lock mechanism, a magnetic lock and a detent, and the controller is arranged to actuate the disassembly mechanism using the actuation element.

In another embodiment, the device includes a resonator attached to the device body, which is arranged to vibrate the arms so as to apply the repetitive motion. The resonator includes at least one element selected from a group of elements consisting of a disk-shaped resonator, a bending resonator, a twist resonator, an electric motor that rotates an eccentric mass, a stepping motor, a piezoelectric exciter, an Electro-Active Polymer (EAP) resonator, an electrostrictive exciter and an electrostatic source. The resonator may be arranged to vibrate the arms with a random vibration having frequencies within a bandwidth containing respective resonant frequencies of the arms.

In yet another embodiment, the arms include at least one material selected from a group of materials consisting of an electrically-actuated material, a piezoelectric material, a Dielectric Elastomer Actuator (DEA), an ionic Electro-Active Polymer (EAP) and an electronic EAP, and the device includes a controller, which is arranged to drive the arms with respective electrical signals so as to cause the arms to apply the repetitive motion. In still another embodiment, the electrical signals have frequencies that approximate respective resonant frequencies of the arms, so as to cause the arms to vibrate at the respective resonant frequencies. Additionally or alternatively, the arms include respective feedback elements, which are arranged to sense vibrations of the arms, and the controller is arranged to adjust respective frequencies of the vibrations of the arms to match resonant frequencies of the arms based on the vibrations sensed by the feedback elements.

In some embodiments, the arms are partitioned into two or more subsets, and the controller is arranged to drive the two or more subsets of the arms in alternation. Additionally or alternatively, the arms may be further arranged to transfer an electrical stimulation to the respective points-of-contact on the inner surface of the organ.

In an embodiment, the device is arranged to discharge a substance within the organ. In some embodiments, the substance is impregnated in at least one of an outer surface of the device body and the arms. Alternatively, the device may include a container holding the substance fitted in the device body. In another embodiment, one or more of the arms include tubes, which are arranged to lead the substance from the container to the inner surface of the organ so as to discharge the substance in a vicinity of the points-of-contact. In yet another embodiment, the device includes a substance discharge mechanism, which is arranged to discharge the substance using at least one effect selected from a group of effects consisting of a chemical reaction, a capillary effect, a pressure effect and a piezoelectric effect. In still another embodiment, the device includes a controller, which is arranged to discharge the substance responsively to at least one of an external command transmitted to the device and a pre-programmed schedule.

In some embodiments, the device includes a transmitter, which is arranged to transmit a status of the device to an external receiver. The transmitter may be arranged to transmit an alert message indicating an appropriate time for externally administering a systemically-acting substance to the patient, in order to enhance a therapeutic effect induced by the repetitive motion and the substance.

In an embodiment, at least one of the device body and the arms include a material that provides visualization when imaged by a medical imaging system. In another embodiment, the arms have curved a-traumatic distal ends. Additionally or alternatively, the arms may have curved profiles so as to increase a structural rigidity of the arms. In another embodiment, the device includes a power source including at least one of a battery, a rechargeable battery and a radio frequency (RF) coil arranged to accept externally-transmitted RF energy.

In yet another embodiment, the device includes a controller, which is pre-programmed with one or more activation profiles defining respective time schedules for activating functions of the device. The functions may include at least one function selected from a group of functions consisting of releasing the arms, applying the repetitive motion, disengaging the arms from the device body, discharging a substance from the device, switching to another activation profile and transmitting a status of the device. Additionally or alternatively, the functions include applying the repetitive motion by the arms and discharging a substance from the device, and the controller is arranged to synchronize a timing of applying the repetitive motion and of discharging the substance, so as to enhance a therapeutic effect induced by the repetitive motion and the substance.

There is also provided, in accordance with an embodiment of the present invention, a system for treating a patient, including:
a transmitter external to the patient, which is arranged to transmit commands using wireless signals; and
a device for insertion into an organ of the patient, including:
a device body;
a receiver fitted in the device body, which is arranged to receive the commands transmitted by the transmitter; and
one or more arms attached to the device body, which are arranged to extend outward from the device body within the organ responsively to a command received by the receiver, so as to contact respective points-of-contact on an inner surface of the organ, and to apply a repetitive motion at one or more of the points-of-contact.

In some embodiments, the transmitter includes a personal control unit.

There is additionally provided, in accordance with an embodiment of the present invention, a system for treating a patient, including:
one or more electromagnets, which are located externally to the patient and are arranged to induce a time-varying magnetic field in an organ of the patient; and
a device for insertion into an organ of the patient, including:
a body, which includes a field-responsive element that is set in motion by the induced time-varying magnetic field; and
one or more arms attached to the body, which are arranged to extend outward from the device body within the organ so as to contact respective points-of-contact on an inner surface of the organ, and to apply mechanical stimulation, whose characteristics depend on the time-varying magnetic field, at one or more of the points-of-contact as a result of the motion of the field-responsive element in the body.

There is also provided, in accordance with an embodiment of the present invention, a method for treating a patient, including:
inserting into an organ of the patient a device including a device body and one or more arms attached thereto in a compact configuration;
causing the arms to extend outward from the device body within the organ so as to contact respective points-of-contact on an inner surface of the organ; and
applying a repetitive motion by the arms at one or more of the respective points-of-contact, so as to cause a therapeutic effect in the patient.

In some embodiments, the therapeutic effect includes at least one effect selected from a group of effects consisting of a systemic physiological effect and a therapeutic effect distant from the organ. In another embodiment, the therapeutic effect includes an alteration of a caloric intake of the patient. In yet another embodiment, the therapeutic effect includes an alteration of a metabolic profile of mucosa in a vicinity of the device.

In still another embodiment, applying the repetitive motion includes inducing a secretion of at least one substance selected from a group of substances consisting of a hormone, a peptide, a cytokine and a molecule by the organ, and the therapeutic effect includes at least one effect selected from a group of effects consisting of an endocrine, an autocrine and a paracrine effect. In a disclosed embodiment, the therapeutic effect includes at least one effect selected from a group of effects consisting of a systemic effect and a local neurally-mediated physiological systemic effect, which is induced via afferent and efferent nervous system fibers.

In another embodiment, applying the repetitive motion includes causing a secretion of at least one substance selected from a group of substances consisting of a hormone, a peptide, a cytokine and a molecule from an organ other than the organ into which the device is inserted. Additionally or alternatively, applying the repetitive motion includes stimulating mechanically-activated tissue receptors at the points-of-contact. Further additionally or alternatively, applying the repetitive motion includes altering a physical tissue property at the points-of-contact. The physical tissue property may include at least one property selected from a group of properties consisting of a permeability, an excitability, a temperature and a consistency at the points-of-contact.

In some embodiments, applying the repetitive motion includes modifying an intra-luminal pressure at the points-of-contact, so as to induce a counter-dilation reaction. Additionally or alternatively, applying the repetitive motion includes affecting a secretion of at least one of a pro-feeding (orexigenic) and an anti-feeding (anorexogenic) hormone in accordance with a treatment profile, so as to control a caloric intake of the patient.

In some embodiments, the method includes administering to the patient a systemically-administered substance that contributes to the therapeutic effect, so as to enhance the therapeutic effect by synergistically using the substance and the repetitive motion. Administering the drug and applying the repetitive motion may include synchronizing a timing of administering the drug and of applying the repetitive motion so as to enhance the therapeutic effect.

The present invention will be more fully understood from the following detailed description of the embodiments thereof, taken together with the drawings in which:

BRIEF DESCRIPTION OF THE DRAWINGS

FIGS. 5A-5E are schematic illustrations of self-extracting arms, in accordance with embodiments of the present invention;

FIGS. 7A-7C are schematic illustrations of a self-extracting and vibrating arm, in accordance with an embodiment of the present invention;

FIGS. 11A and 11B are schematic illustrations of anchoring of a capsule within an intrabody cavity.

DETAILED DESCRIPTION OF EMBODIMENTS

Overview

Figure 1:
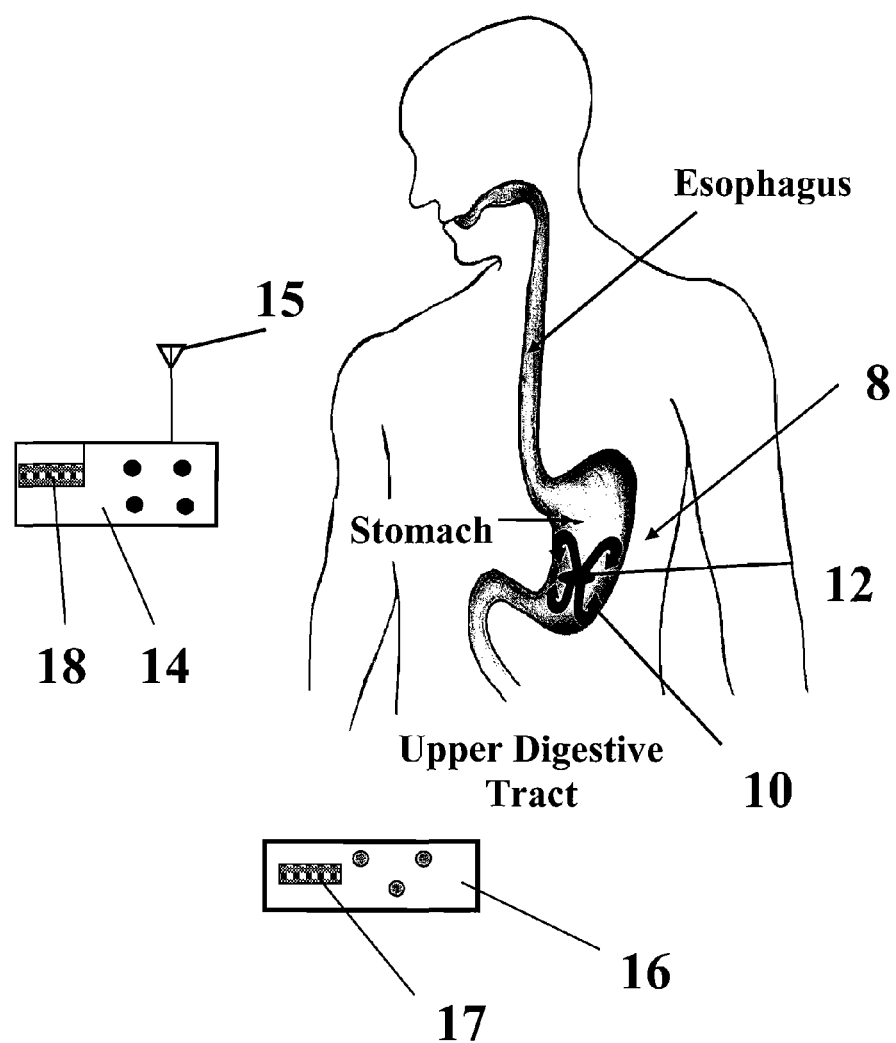
FIG. 1 is a schematic, pictorial illustration of a system for treating obesity, in accordance with an embodiment of the present invention.

Embodiments of the present invention provide improved methods and systems for treating various medical conditions, such as obesity, using intrabody devices inserted into a patient's body. The embodiments described herein mainly address devices inserted into the gastrointestinal (GI) tract, specifically the stomach, in order to reduce caloric intake, although similar intrabody objects can be inserted into other tubular or hollow organs and to treat other conditions, as well.

In some embodiments, a capsule is inserted orally into the patient's stomach. The capsule comprises a capsule body and one or more self-extending arms attached to the body. During insertion, the arms are wrapped around the capsule body or otherwise tightly packed against or within the capsule body, so as to enable smooth and safe passage via the esophagus.

Although the embodiments described herein mainly refer to intrabody capsules, the principles of the present invention can be used in other types of intrabody devices having any suitable shape, size or configuration. For example, intrabody devices other than capsules may be inserted surgically or endoscopically.

When the capsule reaches the desired location in the stomach, the arms are released and allowed to extend, or activated to extend. Several mechanisms for locking and releasing the arms are described herein below. For example, the arms may be held in the collapsed position by a dissolvable cover, which dissolves in the stomach and releases the arms. When extended, the arms come into contact with multiple points on the inner surface of the stomach and anchor the capsule at the desired location.

In some embodiments, the arms may be built as flat thin sheets and be wrapped around the capsule body in concentric layers. Alternatively, the arms can be constructed as cords of various shapes, which are folded on or wrapped around the capsule body in various spirals. For example, the arms may comprise carbon nano-tubes, as are known in the art. The arms can be released to extend, as described hereinbelow, or alternatively be activated to extend by electrical current.

In addition to anchoring the capsule within the location of interest, one or more of the arms apply repetitive motion to the contact points on the inner surface of the stomach. For example, the motion may comprise a sliding motion, a perpendicular pressure motion or a combination thereof. The repetitive motion applied by the arms stimulates the contacted tissue, thus inducing hormonal and neuronal stimulatory effects that suppress the patient's appetite and reduce caloric intake by several possible mechanisms.

In some embodiments, applying the repetitive motion comprises applying vibratory stimulation to the inner stomach surface. For example, the arms (or parts of the arms) may comprise a piezoelectric material, to which the capsule applies a varying electrical voltage in order to vibrate the arms. Generally, the arms may comprise any currently-known or contemplated electrically-actuated material, i.e., a material that translates an electrical actuation voltage to mechanical displacement. For example, material may comprise an ionic or electronic electro-active polymer (EAP) or a Dielectric Elastomer Actuator (DEA), which changes its shape and/or size in response to an electrical signal applied by the capsule. As another example, the arms can be vibrated using a mechanical resonator in the capsule body.

The intrabody capsules described herein can generally be used to alter and control the caloric intake of the patient, either constantly or on a time-varying basis. As will be shown below, the capsule alters the mucosal metabolic and excitatory profile, i.e., affects the metabolism and neuronal output from autonomic neurons and fibers (vagal and splanchnic in the case of the gastrointestinal tract), of the tissue it contacts. Moreover, the local physical stimulation may cause a specific profile of neuronal discharge from the target organ to the central nervous system, thus inducing systemic effects.

In some embodiments, the capsule is controlled by an external operator console, which transmits commands to a receiver in the capsule. For example, the capsule can be activated and instructed to expand using an external command. The capsule comprises a computerized customizable controller that can be activated by the external commands to perform pre-programmed functions and additional functions at will. When desired, the capsule can be instructed to disassemble, or alternatively to fold its arms back to their initial compact position, by an electric activation signal.

When the capsule is instructed to disassemble, a disassembly mechanism separates the arms from the capsule body, and the different capsule elements are naturally disposed of via the patient's digestive system. All elements of the device are thus able to advance passively, distal from its location of activity. When the arms are folded back, the entire capsule system will be naturally disposed off without the need for disassembly. In other organs, the elements of the device may be evacuated naturally or by surgical means, depending on the organ or system involved.

Several exemplary configurations of self-extending capsules are described herein below. Additionally or alternatively to applying tissue stimulation, in some embodiments the capsules perform additional functions. For example, a capsule may perform localized administration of medications and other substances.

In some cases, the operation of the intrabody capsule can be combined with a systemic administration of a drug. The systemic effects induced by the capsule can enhance similar specific effects induced by the drug, and vice versa. The intra-gastrointestinal stimulation provided by the capsule can also be useful in promoting insulin secretion, such as in patients having altered glucose metabolism.

The tissue stimulation applied to the inner surface of the stomach can be combined with an electrical stimulation, which is applied by the arms. For example, the arms can be made of un-coated, electrically conductive material. A power source in the capsule body can apply an electrical signal to the contact points on the stomach surface via the electrically-conductive arms.

In another embodiment of the present invention, a device is inserted into the stomach using laparoscopic surgery, surgical laparotomy or laparoscopy or other minimally invasive means. Devices inserted in this manner can be made larger than swallowable capsules, and therefore may be designed to apply more intense stimulation and/or to apply stimulation for a longer time duration.

In some embodiments, the repetitive motion of the device is actuated and controlled by external magnetic induction. In these embodiments, the device body comprises a natural magnet, an iron element or any other element that can be set in motion by applying an external magnetic field. A time-varying magnetic field is applied in the vicinity of the capsule. The device vibrates or is otherwise set in motion in response to the magnetic field, thus applying repetitive motion to the points of contact on the inner stomach surface. Signals can be transmitted to a magnetic switch inside the device.

System Description

FIG. 1 is a schematic, pictorial illustration of a system for treating obesity, in accordance with an embodiment of the present invention. A miniature capsule 8 (also referred to as a device) is swallowed or inserted orally via the mouth and the esophagus, into the patient's stomach. The device may either be swallowed by the patient or be inserted using an endoscope.

The device comprises a capsule body 12 and one or more self-extending arms 10, which may have various dimensions, sizes, constructions and material composition. The different capsule elements are typically bio-compatible and a-traumatic. During insertion of the device, arms 10 are folded, wrapped, collapsed or otherwise tightly packed adjacently to the device body, in order to enable the device to safely and conveniently pass through the esophagus. At a desired location within the patient's body, such as upon reaching a particular location in the stomach, the arms self-extract to their expanded form. Typically, the device comprises multiple arms, which extract and contact the inner surface of the stomach at multiple points, thus anchoring the capsule at the desired location and preventing it from advancing distally within the lumen.

When swallowed or inserted, the capsule is tightly packed into a cylindrical or oval shape, so as to enable easy and safe insertion via the patient's esophagus. In its packed form, the capsule has a typical diameter of 8-12 mm and a typical length of 15-30 mm. When extended, each arm has a typical span of up to 60 mm. The dimensions indicated are given by way of example, and any other suitable dimensions can be used, depending on the organ and location of interest. In some cases, the arms may differ from one another in their dimensions, construction, shape and/or material composition. The device dimensions may vary depending on its contents, route of insertion and configuration. Several exemplary device configurations are described in detail in FIGS. 3A-11 below.

Capsule body 12 may comprise any suitable material, such as metal or plastic. Arms 10 may also comprise materials such as metal or plastic. In some embodiments, the arms, or parts of them, comprise piezoelectric materials, ionic or electronic electro-active polymers (EAP) or Dielectric Elastomer Actuators (DEA), so as to enable the arms to move and vibrate, as described below.

In some embodiments, insertion of the capsule is visualized using an imaging system, such as an ultrasound imaging system, an x-ray imaging system or any other suitable imaging modality. The imaging system enables a caregiver, such as a physician, to track and verify the location of the capsule in the body. For this purpose, the capsule may comprise material that is clearly visible to the imaging modality used.

Capsule 8 is controlled by an external console 14. Console 14 comprises an input device, such as a keypad 18, using which the caregiver enters commands for controlling the capsule. A transmitter inside console 14 translates the commands into control signals and transmits the control signals via a transmit antenna 15 to a miniature receiver (shown in FIG. 2 below) fitted in the capsule. The transmitter typically transmits a low power signal, and the antenna is typically positioned in close proximity to the patient body, in order to eliminate effects on neighboring patients who may have a similar capsule operating in their body and to minimize the need for different frequencies to be used by different transmitters. In an alternative embodiment, different transmitter-capsule pairs may use different frequencies.

In some embodiments, the caregiver can activate the capsule, i.e., instruct the capsule to expand, by transmitting an appropriate command from console 14. The caregiver may track the capsule using the imaging system as it travels through the gastro-intestinal tract. When the capsule reaches the location of interest, in this case the patient's stomach, the caregiver instructs the capsule to expand. The capsule receives the command and releases arms 10 to their expanded position. As a result, the capsule anchors at the desired location.

Once anchored and activated, the capsule can be used to create local and systemic effects through several mechanisms. The distal ends of arms 10, which are in contact with the gastrointestinal mucosa (in this case—the inner lining surface of the stomach), apply repetitive motion to the points of contact, as will be explained in detail below. The repetitive motion causes tissue stimulation, e.g., vibratory, tactile, mechanical and/or nociceptive stimulation.

In some embodiments, the repetitive motion has a frequency on the order of several tenths of a Hertz and up to many tens of Hertz. A typical range of motion, or displacement amplitude of the arms, is on the order of several microns and up to many millimeters. In some cases, the repetitive motion is applied in intermittent sessions, such as for several tens of seconds in each half hour. Alternatively, however, any other suitable frequency and displacement values, and any constant or intermittent activation patterns and duty cycles can be used.

Thus, in the context of the present patent application and in the claims, the term "repetitive motion" is used to describe any sort of repetitive displacement of the arms, which may have any desired frequency, spectral content, magnitude, duty-cycle, pattern and/or operating schedule. Typically but not necessarily, the repetitive motion may comprise a sliding motion, a tilting motion, a perpendicular pressure motion or a combination thereof.

The points of contact on the inner stomach surface are often dispersed over a large surface area. The various modes of stimulation applied by the arms to the tissue may stimulate neuronal receptors as well as other elements of the inner gastrointestinal mucosa and thus cause or facilitate secretion of hormones having both local and peripheral effects, ultimately leading to reduced caloric intake. Similarly, stimulation of local receptors and nerve endings within the tissue in proximity to the arms will create a neuronal discharge to the central nervous system, thus causing systemic effects in multiple physiological systems. These effects may include, but are not limited to, effects on gastro-intestinal motility, hormone secretion and the feeling of satiety.

In some embodiments, arms 10 are vibrated in order to cause vibratory tissue stimulation. For example, the expanded capsule structure may be vibrated at a frequency that is close to the resonant frequency of one or more of the arms, or at the resonant frequency of the entire capsule. Typically, the arms are expected to have a resonant frequency in the range of 0.1 to 50 Hz. Vibrating the arms can be carried out using a resonator within the capsule, for example, or using arms made partially or fully of piezoelectric materials, electro-active polymers or dielectric elastomer actuators. An exemplary capsule configuration comprising a resonator is described in FIG. 6 below. Exemplary arms made of piezoelectric materials or electro-active polymers are shown in FIGS. 5A-5E and 7A-7C below. It should be noted that the tissue stimulation effects described above are significantly stronger, more prominent and independent of the effect of the physical dimension of the extended device per se, in causing the desired physiological effects.

The stimulation applied to the tissue by the arms may cause several effects. In some cases, a nociceptive stimulation of tissue creates a discharge of hormones, peptides and/or cytokines having endocrine, autocrine and/or paracrine effects. Additionally or alternatively, applying light pressure on tissue of interest creates neurally-mediated physiological systemic and/or local effects via afferent and efferent autonomic fibers. Applying pressure by the arms may also affect mechanically-activated tissue receptors, producing systemic and/or local effects. Further additionally or alternatively, applying local tissue contact may alter the physical tissue properties such as permeability, temperature and surface texture. Furthermore, a localized contact with tissue typically alters its volume and changes its intra-luminal pressure, thus inducing a counter-dilation reaction.

In some cases, the tissue stimulation produced by capsule 12 may reduce the secretion of orexogenic hormones, such as gherlin and other peptides or molecules, by imitating a constant presence of an undigested element in the stomach. The nociceptive or light tactile stimulation may also induce the secretion of hormones from the distal gastrointestinal tract, such as PYY 3-36, GLP-1, enterostatin, oxyntomodulin, CCK or other peptides or molecules, which inhibit food intake.

In some embodiments, the capsule can locally discharge various substances that affect the gastro-intestinal tract locally or the central nervous system and aid in suppressing the patient's appetite. These substances may induce local and distal effects of chemical substances, hormonal and neural discharge. Such substances may comprise any suitable chemical substance, such as a molecule, peptide, protein or other pharmacologic substance having an appetite suppression effect. For example, the administered substance may comprise a fatty acid derivative such as linoleic acid, or a hormonal receptor agonist that will cause an anorexogenic effect. Some peptides that can be discharged by the capsule may induce the secretion of gut hormones, such as cholecystokinin (CCK), from the upper gastrointestinal tract, thus reducing caloric intake.

Figure 10:
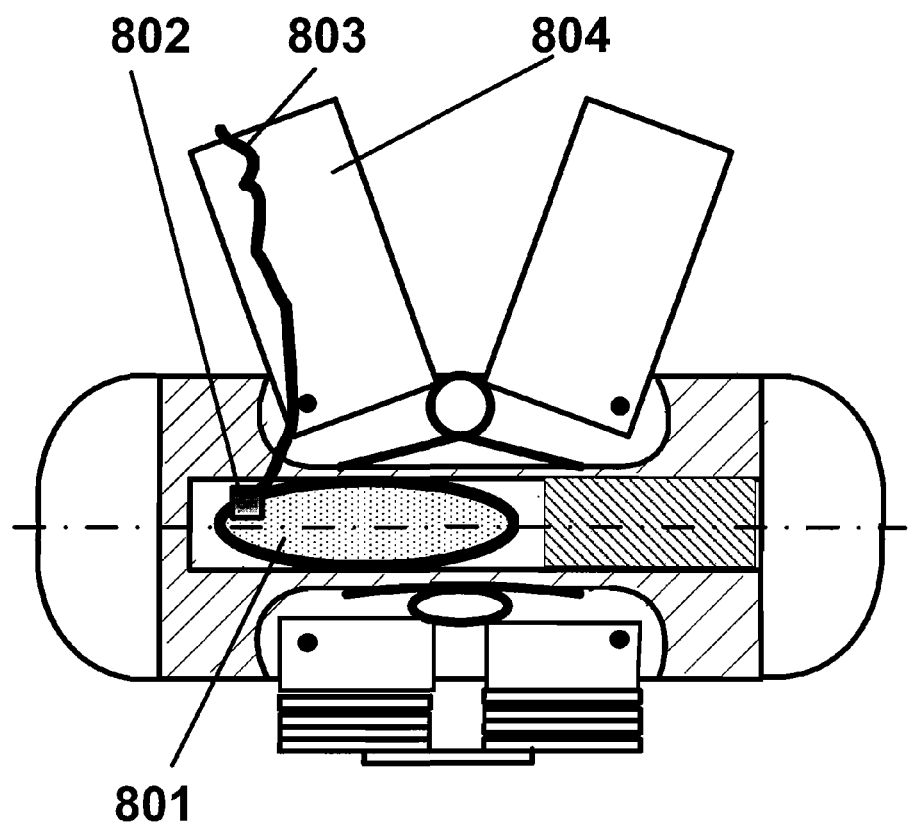
FIG. 10 is a longitudinal cross-section of an intrabody capsule, in accordance with an alternative embodiment of the present invention.

Since the capsule delivers the substance locally, extremely small quantities of the substance are sufficient for inducing the desired effect. In some embodiments, the capsule comprises a container containing the relevant substance. An example of such a configuration is shown in FIG. 10 below. In other embodiments, the device may contain a larger substance reservoir. Further alternatively, the outer surface of the arms and/or the capsule body may be impregnated with the substance. In these embodiments, the substance is released using the endogenous motion of the arms and the capsule or by a sustained release mechanism.

In some embodiments, the tissue stimulation and/or substance discharge can be controlled and customized. Physical tissue stimulation and/or substance administration can be activated and deactivated on demand by transmitting commands from the external console to match a desired treatment profile. Thus, the caregiver is able to alter the treatment profile over time and to customize the profile to the needs of a particular patient. Altering the treatment profile also helps to reduce adaptation and resistance to the treatment by the patient's body. Alternatively, a particular treatment profile can be pre-programmed in the capsule.

In order to remove capsule 12 from the patient's body, the capsule comprises a disassembly mechanism, which causes arms 10 to disengage from capsule body 12. The disassembly mechanism can be activated, for example, in response to a command transmitted from external console 14. Additionally or alternatively, the disassembly mechanism can be activated after a pre-programmed time interval, when the capsule power source is close to exhaustion or reaches a certain capacity threshold, when the substance administered by the capsule runs out or when any other suitable condition is fulfilled.

Once disassembled, the different capsule elements pass through the digestive tract naturally and are excreted through the patient's digestive system. Typically, the different parts of the capsule comprise materials that can be clearly imaged by the imaging modality used (e.g., ultrasound), so that the caregiver is able to verify that no parts remain in the body. The different capsule elements are typically made of biocompatible materials.

Additionally or alternatively, some aspects of the treatment profile can sometimes be controlled during everyday use, such as by the patient. For example, in some embodiments the patient is provided with a personal control unit 16, which allows control over the operation of capsule 8. Unit 16 comprises an input device, such as a keypad 17, for this purpose. Typically, the personal control unit comprises a subset of the functions and elements of console 14. For example, the patient can use the personal control unit to activate and deactivate the vibration of arms 10, in order to enable normal caloric intake at certain times and reduce caloric intake at other times. Providing access to other functions of the personal control unit is customizable and user-dependent, enabling different users to have access to different sets of functions and activities of the device. Activating the capsule disassembly may or may not be enabled in unit 16.

In some embodiments, unit 16 comprises a low-power transmitter, which communicates with the capsule when the unit is in touch with, or in proximity to the patient body. Additionally or alternatively, the functionality of unit 16 can be embodied in a suitable communication or computing device, such as a mobile phone or a handheld computer.

Figure 2:
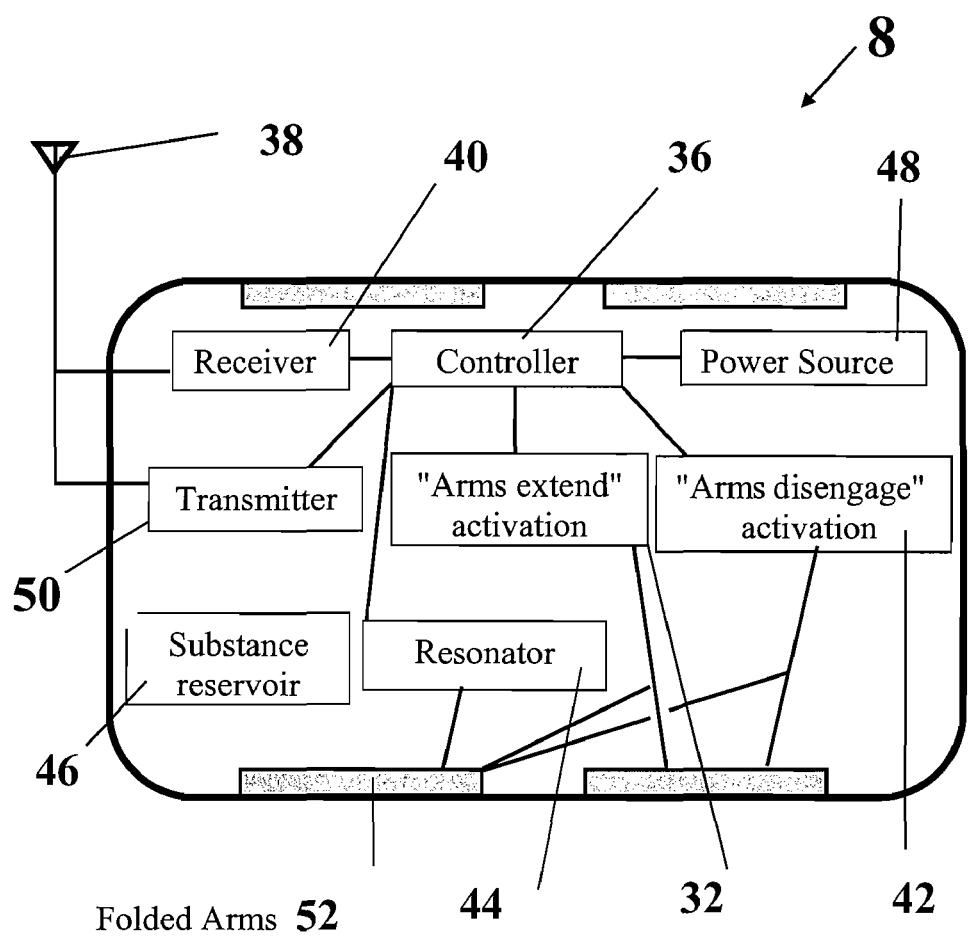
FIG. 2 is a block diagram that schematically illustrates functional components of an intrabody capsule, in accordance with an embodiment of the present invention.

FIG. 2 is a block diagram that schematically illustrates functional elements of capsule 8, in accordance with an embodiment of the present invention. Some elements in FIG. 2 are optional, i.e., different configurations of capsule 8 may comprise only a subset of the elements. Several exemplary capsule configurations are described in detail further below.

Capsule 8 comprises a controller 36, which manages the operation of the capsule and activates its elements. Controller 36 may comprise a microprocessor running suitable software code. Alternatively, the controller may be implemented using hardware or firmware, such as using an application specific integrated circuit (ASIC) or field programmable gate array (FPGA). Further alternatively, the controller may be implemented using a combination of hardware and software functions. Typically, the controller comprises one or more pulse generators, voltage up-converters or other drivers that activate the different capsule elements, including the piezoelectric functions. In some cases, the controller comprises power management circuitry for selectively activating and deactivating elements of the capsule in order to reduce its energy consumption.

Capsule 8 comprises an antenna 38 and a receiver 40, which receive the control signals transmitted from console 14. (In the description that follows, external commands are described as being transmitted by console 14. As noted above, these commands may similarly be transmitted by personal control unit 16.) The receiver decodes the transmitted commands and provides them to controller 36. The capsule further comprises an arms extend activation module 32 and an arms disengage activation module 42.

When instructed by controller 36, module 32 releases self-extending arms 10 so as to enable them to open to their expanded position. When instructed by the controller, module 42 disassembles the arms from their base, thus disengaging the arms from the capsule body, to allow the capsule to leave the body. In general, releasing and/or disassembling the arms can be triggered by different conditions, such as after a predetermined time or based on an external command. Exemplary release and disassembly mechanisms are shown in detail in FIGS. 8A, 8B, 9A and 9B below. In some embodiments, the release mechanism comprises a dissolvable cover that holds the arms in their compact, packed position. When the cover dissolves in the stomach, the arms are free to release. Such a configuration is addressed in FIG. 8A below.

In some embodiments, capsule 8 comprises a resonator 44, which vibrates the expanded capsule structure, as described above. Resonator 44 may comprise a commercial disk-shaped resonator, a bending resonator, a twist resonator, an electric motor that rotates an eccentric mass, a stepping motor, a piezoelectric exciter, an electro-active polymer based resonator, an electrostrictive exciter, an electrostatic source or any other suitable resonator known in the art. The resonator is activated and deactivated by controller 36. Alternatively, e.g., when capsule 8 comprises piezoelectric arms, the arm vibrations are activated, generated and deactivated by controller 36, as preprogrammed, or alternatively triggered by the console 14 or unit 16.

Controller 36 may be pre-programmed with one or more treatment profiles. Each treatment profile comprises a sequence of capsule operations, such as physical stimulation and/or substance discharging operations, which are performed in a certain time schedule. The appropriate treatment profile can be programmed or selected before the capsule is inserted into the patient body. When multiple profiles are pre-programmed in the controller, a different profile can also be selected by transmitting a suitable external command to the capsule from console 14 or from unit 16.

In some embodiments, the capsule comprises a miniature substance reservoir 46, which holds a substance that is locally administered by the capsule. The discharge of substance from reservoir 46 is activated and deactivated by controller 36. An exemplary configuration comprising a substance reservoir is shown in FIG. 10 below.

In some embodiments, capsule 8 comprises a transmitter 50, which transmits data provided by controller 36 to an external receiver (not shown). The data transmitted by transmitter 50 may comprise, for example, acknowledgements of the external commands received and performed by the capsule. Additionally or alternatively, the transmitter may transmit telemetry and status data such as battery status and failure indications, and/or any other suitable information of interest. In the configuration of FIG. 2 the transmitter uses antenna 38 for transmitting the data, although in alternative configurations separate transmit and receive antennas can also be used.

Capsule 8 comprises a power source 48, which supplies electrical power to the different capsule elements. Power source 48 may comprise one or more redundant batteries for enhancing capsule reliability. In some embodiments, controller 36 is able to monitor the voltage and/or current of the power source, so as to sense when the power source is weak or exhausted. Power source 48 can also be used for applying electrical stimulation to the contact points on the inner stomach surface via the arms.

In an alternative embodiment, some or all of the energy for powering capsule 8 can be provided by transmitting radio frequency (RF) energy to the capsule. RF energy is typically transmitted using an external coil, which may be worn by the patient or be part of console 14 or unit 16. The RF transmission may be used to power the capsule directly and/or to charge a battery in the capsule. In these embodiments, power source 48 comprises a suitable coil for receiving the transmitted RF energy, as well as suitable rectification circuitry, as is known in the art.

Intrabody Device Configurations

FIGS. 3A-11 below show several exemplary mechanical configurations of self-extracting intrabody devices and some of their internal mechanisms.

Figure 3A:
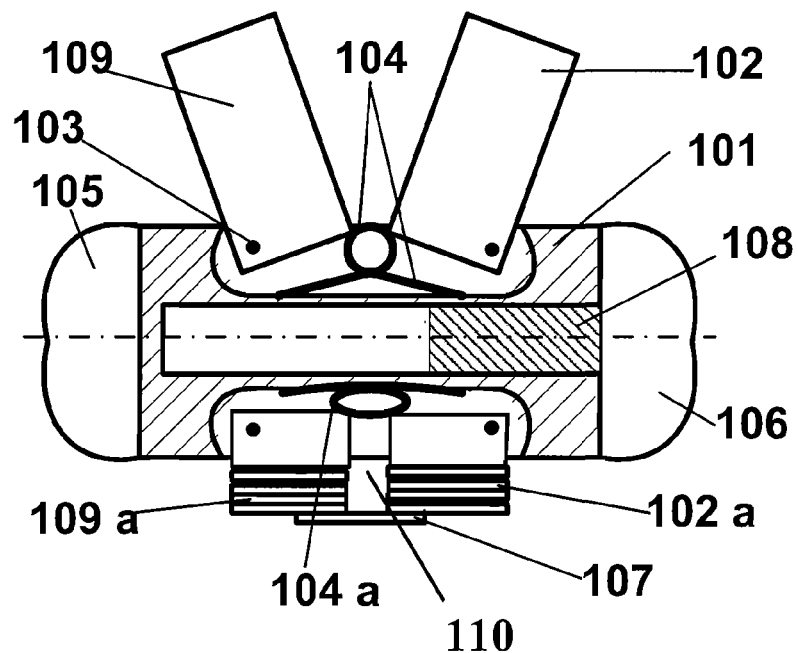
FIGS. 3A, 3B, 4A and 4B are longitudinal and transverse cross-sections of intrabody capsules, in accordance with embodiments of the present invention.

FIG. 3A is a longitudinal cross-section of an intrabody capsule, in accordance with an embodiment of the present invention. The capsule comprises a capsule body 101, comprising metal, plastic or any other suitable material. Two arms 102 and 109 are shown fully-extended. Two arms 102A and 109A are tightly wrapped around the capsule body. The arms may comprise any suitable elastic material, such as various metals and plastics, or a combination thereof. In some embodiments described below, the arms, or a part of them, comprise a piezoelectric material, an electro-active polymer or a dielectric elastomer actuator. The arms are constructed so that their natural, unrestrained state is extended. In other words, when no force is applied to the arms, the arms will remain in the extended position.

In alternative embodiments, such as when the intrabody device is inserted surgically or endoscopically, the configuration of the device can be larger and different from a capsule configuration.

Arms 102A and 109A are shown wrapped several times around the capsule body. Each arm is fastened to capsule body 101 so as to rotate around a respective pivot 103. The wrapped arms are pressed against a compressed spring 104A and held by a lock/release mechanism 110. The lock/release mechanism comprises a pin, a latch and a cover 107. One or more such mechanisms lock the folded arms to the capsule body. Cover 107 may comprise one or more thin parts made of metal, polymer and/or fabric. Exemplary lock/release mechanisms are shown in greater detail in FIGS. 8A, 8B, 9A and 9B below.

The latch of mechanism 110 is actuated to release the arms by a controller 108, similar to controller 36 of FIG. 2 above. The latch can be actuated using a shape memory alloy (SMA) element, a motor, a piezoelectric element, an electro-active polymer element, a solenoid, an electro-mechanical detent, a magnetic lock, or using any other suitable actuation device known in the art. When the latch is actuated, the pin of mechanism 110 is pushed out of the capsule, releasing cover 107 and allowing the arms to extend. Spring 104A further pushes the arms to rotate around pivot 103 until the arms reach the fully-extended and sidewise-tilted positions. A spring 104 is shown in its uncompressed form, with arms 102 and 109 fully extended. Spring 104 is shown as a central helical torsion spring, although a leaf spring, a torsion spring on pin 103 or any other suitable spring known in the art can also be used.

When extended, arms 102 and 102A are located in a certain position, and arms 109 and 109A are located in a different position. As can be appreciated, the distal ends of arms 102 and 109 are distant from one another, thus providing both anchoring and tissue stimulation over a set of widely-dispersed points on the inner stomach surface. A receiver and antenna 106 and a battery 105 are also shown. The distal ends of arms 102 and 109 are curved and a-traumatic (not shown), so as to avoid tissue damage and blocking of orifices.

Figure 9A:
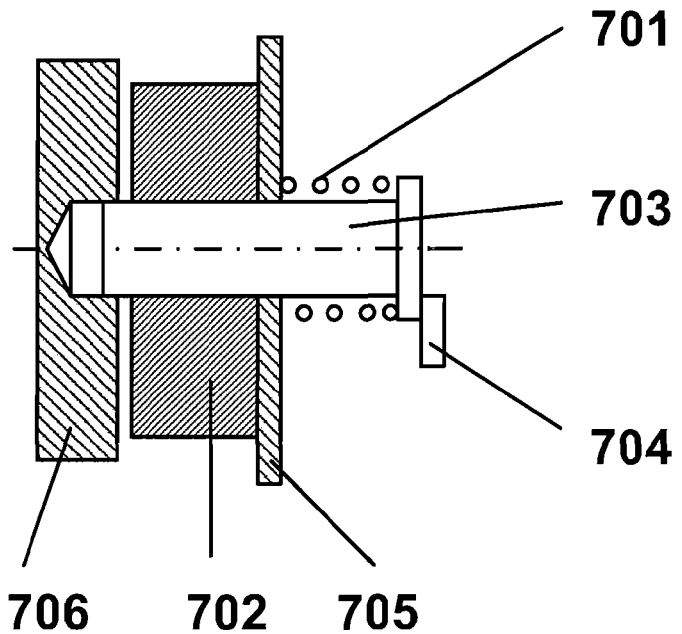
FIGS. 9A and 9B are cross-sections of lock and release mechanisms of self-extracting arms, in accordance with embodiments of the present invention.
Figure 9B:
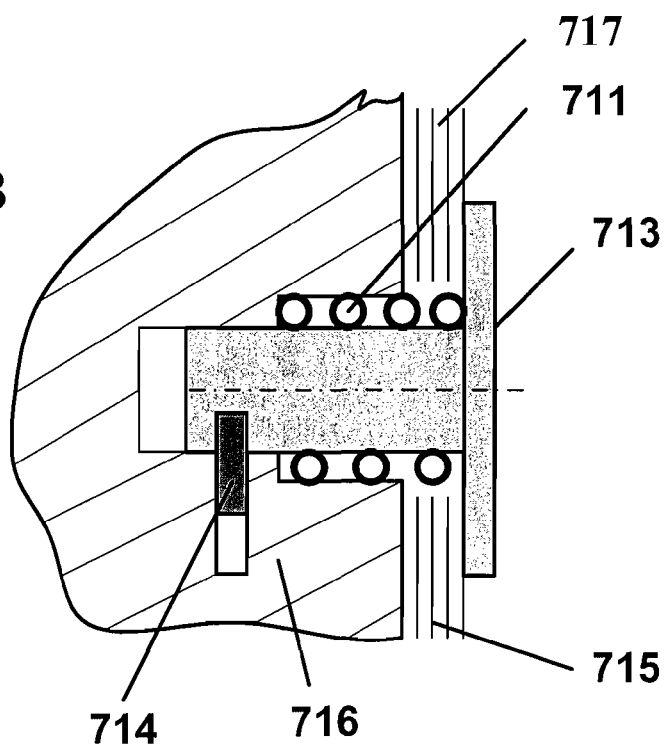

In some embodiments, pivot 103 is also used as part of the capsule disassembly mechanism. When instructed by the controller, the disassembly mechanism removes pivot 103 from its place. As a result, the arm is disconnected from the pivot and disengages from the capsule body. Exemplary disassembly mechanisms are shown in FIGS. 9A and 9B below.

In alternative embodiments, the bases of the arms can be attached to the capsule body using other types of attachment mechanisms, which are releasable and can thus be part of the disassembly mechanism. For example, the arm bases can be attached to the capsule body using a pin, a friction mechanism, a tapered (conical) locking mechanism, or using any other suitable releasable attachment mechanism.

Figure 3B:
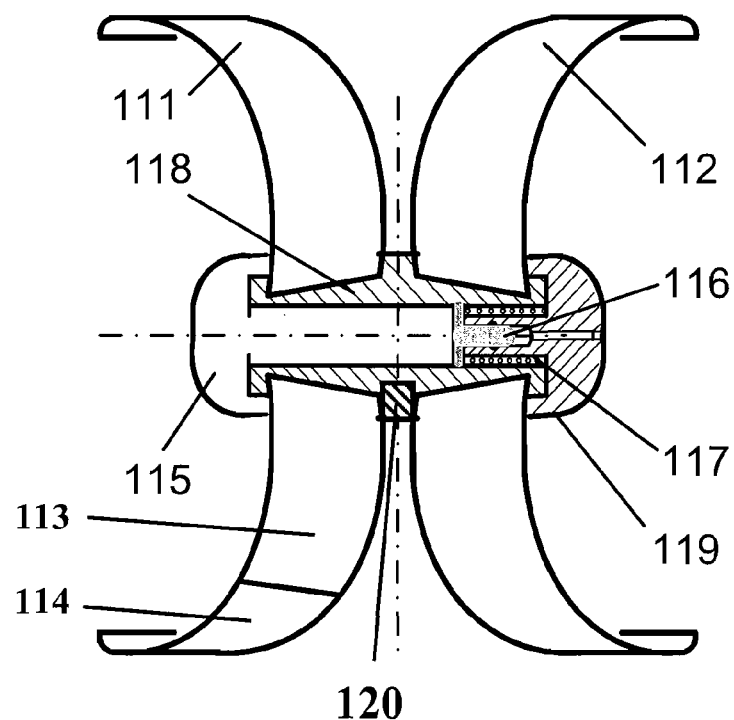

FIG. 3B is a longitudinal cross-section of an intrabody capsule, in accordance with another embodiment of the present invention. In the present example, arms 111 and 112 comprise flexible curved arms that are wrapped over conically-shaped parts 118 of the capsule body. Thus, when the arms are released they unfold into curved shapes having distal ends that are distant from one another, without requiring the use of springs as in the embodiment of FIG. 3A above.

Arms 111 and 112 may comprise any suitable elastic material, such as various metals and plastics or a combination of such materials. In some embodiments, the arms or a part of them comprise a piezoelectric material, an electro-active polymer or a dielectric elastomer actuator, so that they can be electrically controlled and vibrated without the use of springs or other resonators in the capsule. The distal ends of arms 111 and 112 are curved and are designed to be a-traumatic, so as not to damage the tissue in their vicinity or block natural orifices.

In another embodiment, one or more of the arms may comprise a proximate part 113, which is made of a flexible material as described above, and a distal part 114, which is made of a piezoelectric material, EAP or DEA (commonly known as "Artificial Muscles").

A disassembly ball-lock mechanism 116 comprises springs 117. When actuated, the balls release domes 115 and 119. Two springs 117 then push the two domes outwards along the central axis of the capsule. Alternatively, with the domes can be pushed out using only one spring. The movement of the domes frees the arms to disengage from the capsule body.

In an alternative embodiment, which is shown at the bottom of FIG. 3B, the inner part of the arms is kept in place by a ring-shaped element 120, of which only half is visible in the figure. Element 120 is made of two or more parts, which are locked by a ball lock mechanism, locked by the flexibility of the ring itself that is later released, or locked by any other suitable locking mechanism known in the art. The two or more parts of ring-shaped element 120 are preloaded by one or more springs. When released, the ring-shaped element disassembles into the two or more parts and is pushed out forcibly by the springs. As a result, one side of each arm is released and the arms disengage from the capsule body. When using this embodiment, the domes can be made rigid, leaving more room for other elements of the capsule.

As noted above, mechanism 116, or alternatively the mechanism that locks element 120, can be actuated by a SMA element, a motor, a piezoelectric element, an electro-active polymer (EAP) element, an electro-mechanical detent, a magnetic lock, a solenoid or any other suitable actuation device. In the present example, mechanism 116 comprises a ball-lock mechanism. Alternatively, mechanism 116 may comprise any other suitable locking mechanism known in the art.

Figure 4A:
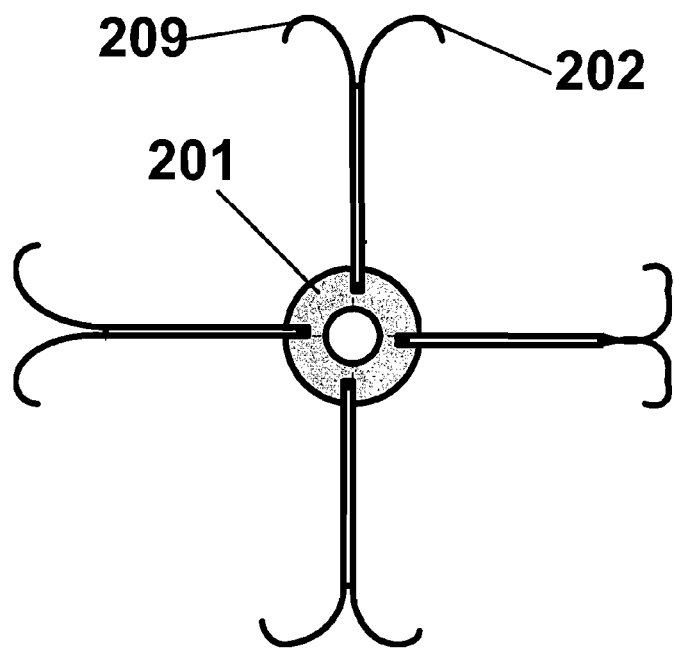

FIG. 4A is a transverse cross-section of an intrabody capsule, in accordance with an embodiment of the present invention. The figure shows the capsule with its arms in the fully extended position. In the present example, eight arms are attached to a capsule body 201. Two arms 202 and 209 are shown curved in different directions, although each of the eight arms may alternatively be curved in any desired direction or plane. The curvature of the distal ends of the arms helps to prevent tissue damage or blockage of orifices. When folded, the arms are wrapped around the perimeter of capsule body 201 and held in place by a suitable lock/release mechanism (not shown).

Figure 4B:
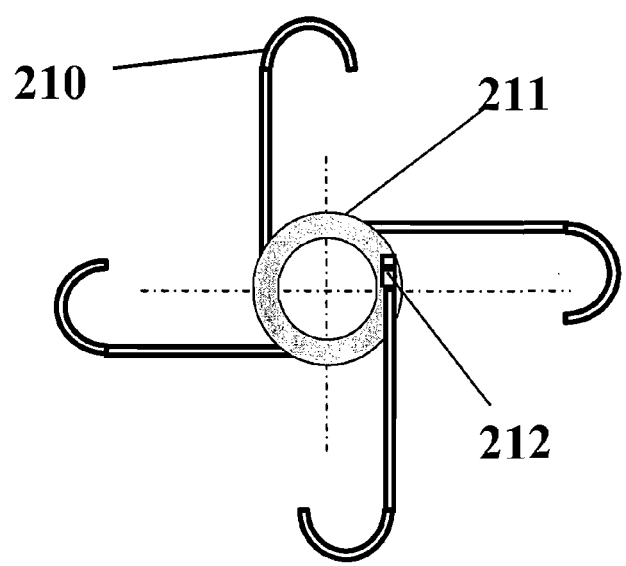

FIG. 4B is a transverse cross-section of an intrabody capsule, in accordance with another embodiment of the present invention. Unlike the configuration of FIG. 4A above in which the arms bases are perpendicular to the surface of the capsule body, in the present example arms 210 are tangent to a capsule body 211. The tangent arm configuration reduces the strain at the point of connection between the arms and the capsule body when the arms are in the folded position. The tangent arm configuration may also simplify and smoothen the disengagement of the arms when the capsule is disassembled.

The disassembly mechanism of the capsule of FIG. 4B comprises two domes or caps (not shown), similar to domes 115 and 119 of FIG. 3B above. Each arm 210 comprises a base 212. When the domes are pushed aside during disassembly of the capsule, bases 212 are free to disengage from capsule body 211 so as to separate the arms from the body. Alternatively, the capsule of FIG. 4B may comprise a disassembly mechanism that uses a ring-shaped element, similar to element 120 of FIG. 3B above. When the ring-shaped element is released, the arms are freed to disengage from the capsule body.

FIG. 5A is a schematic frontal view of a self-extending arm 309, in accordance with an embodiment of the present invention. Arms of this kind can be used, for example, in the capsule configurations of FIGS. 3A, 4A and 4B above. Arm 309 comprises a flexible, elastic material such as metal, plastic, EAP, DEA or piezoelectric material, or a combination of these materials.

In some embodiments, some of the arms are used for anchoring the capsule and other arms are used for applying stimulation using repetitive motion. Some of the arms may be used for both purposes. When a particular arm is used for anchoring only, the arm may be made of metal or plastic. Arms used for applying stimulation may be constructed using a combination of materials. Additionally or alternatively, some or all of the arms may be used for local delivery of substances.

FIGS. 5B and 5C respectively show side and top views of arm 309. As can be seen in FIG. 5C, the arm has a slightly curved profile 301 along its entire length, so as to provide some structural rigidity to the arm when extended. The curved profile of the arm is flattened when the arm is wrapped around the capsule body. Alternatively, other stiffening geometries can also be used. As shown in FIG. 5B, the arm comprises a thickened bottom section 315, which provides a firm attachment to the capsule body. The bottom section comprises a pivot 303, similar to pivot 103 of FIG. 3A above.

FIGS. 5D and 5E are schematic illustrations of a self-extending arm 316, in accordance with an alternative embodiment of the present invention. FIG. 5D is a frontal view, and FIG. 5E is a side view of arm 316. In the present example, the arm has curved sides, so as to enable the arm to be wrapped around a conical part of the capsule body, and then spread outward longitudinally when released, as shown in FIG. 3B above. Arm 316 is stiffened using a curved profile along its entire length, similarly the profile shown in FIG. 5C above.

Arm 316 typically comprises a suitable piezoelectric material, as described further herein below, but may alternatively be made of metal, EAP, DEA or plastic material, or a combination thereof. When made of piezoelectric materials, the arms may comprise a feedback element, which enables the controller to regulate the vibration in the resonance frequency of each arm separately. The feedback mechanism is described in greater detail further below.

The bottom section of arm 316 comprises one or more cantilever extensions. In FIG. 5D, two extensions denoted 317 and 318 are shown. The extensions are fitted into respective cavities (not shown) in the capsule body and domes, and anchor the arm to the capsule body. Typically, the extensions facing the perimeter of the capsule body have rounded ends.

When the capsule is to be disassembled, the domes are pushed aside and the extensions are free to eject out of the cavities, so as to disengage the arms. These extensions may also be used for providing electrical contacts leading to the electrically-conducting parts of the arms, whose use is explained below.

Figure 6:
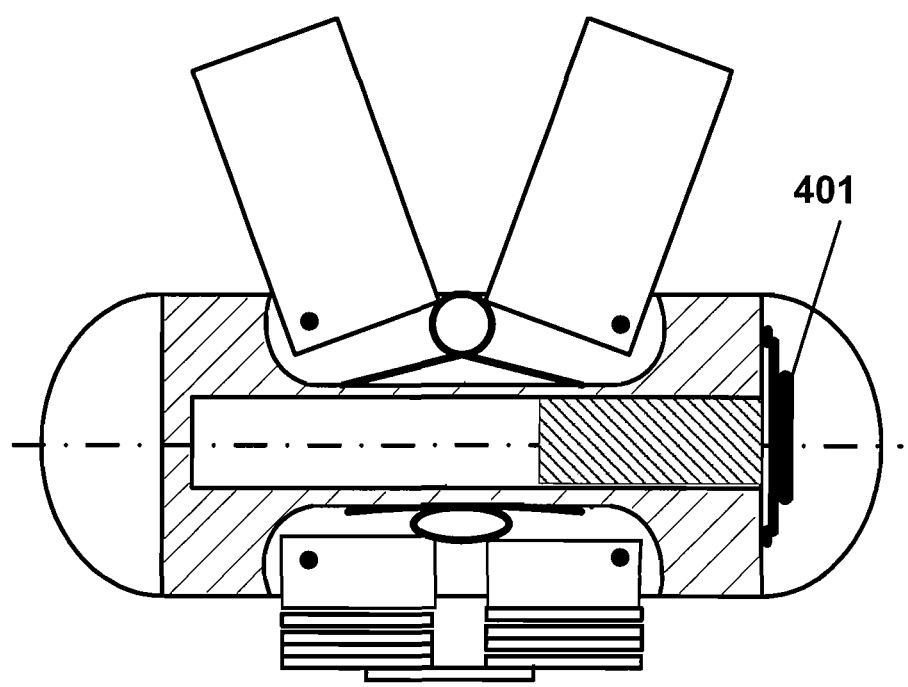
FIG. 6 is a longitudinal cross-section of an intrabody capsule, in accordance with yet another embodiment of the present invention.

FIG. 6 is a longitudinal cross section of an intrabody capsule, in accordance with yet another embodiment of the present invention. A resonator 401, in the present example comprising a piezoelectric disk, is fitted in the capsule body. Alternatively, any other suitable resonator can be used. As explained above, the resonator vibrates the extended arms, typically at a frequency near the resonant frequency of the arms or of the entire device.

In many cases, each arm has a slightly different resonant frequency. Thus, in some embodiments, the resonator is actuated to produce random vibrations within a relatively narrow frequency band that is expected to include the different resonant frequencies of the arms. Although resonator 401 is shown fitted in a capsule similar to the configuration of FIG. 3A above, similar resonators can be fitted in any other suitable capsule configuration.

FIGS. 7A-7C are schematic illustrations of a self-extending and vibrating arm 509, in accordance with an embodiment of the present invention. FIG. 7A is a frontal view, FIG. 7B is a side view and FIG. 7C is a top view of arm 509. The geometry of arm 509 is similar to the geometry of arm 309 of FIGS. 5A-5C above, although any other suitable arm geometry can be used. Arm 509 comprises (i.e., is at least partially made of) a piezoelectric material, an ionic or electronic EAP material or a DEA material.

In order to generate vibration, controller 36 applies an alternating current (AC) voltage to the piezoelectric material of the arm. As a result of the piezoelectric effect, the arm vibrates in accordance with the frequency of the AC voltage.

The material may comprise a piezoelectric polymer such as Polyvinyldifluoride (PVDF), a composite material such as macro-fiber composite (MFC), or any other suitable material having piezoelectric properties. The arm may be constructed as a uni-morph, a bi-morph or any other suitable piezoelement known in the art. The piezoelectric effect may cause the arm to twist, bend, extend or otherwise modify its shape.

In some embodiments, the arm may comprise an electroactive polymer (EAP) or a Dielectric Elastomer Actuator (DEA), also known as an "artificial muscle." The material used may comprise an electronic EAP, which is activated by an electrical field or a Coulomb force, or an ionic EAP, which is activated ionically and/or electrolytically. Electronic EAPs, for example, dielectric elastomer EAPs, ferroelectric polymers, electrostrictive graft elastomers and electrostrictive paper EAPs. Ionic EAPs may comprise, for example, Ionic Polymer Gels (IPG), Ionomeric Polymer-Metal Composites (IPMC), conductive polymers and carbon nanotubes. The material may also comprise ferroelectric EAPs, liquid crystals, Graphite-based polymers, Electro-Rheological Fluids (ERF) or any other suitable electroactive material or structure.

In some cases, the arm may comprise a combination of two or more materials. For example, in some embodiments, only the distal section of the arm (typically 10-15 mm in length) comprises an EAP, a DEA or piezoelectric material that is set in motion by the controller. The remaining part of the arm, which is not in touch with the inner stomach surface, can be made of any suitable elastic material, such as a polymer or metal. In these embodiments, the arms deploy and anchor using their inherent elasticity, and the distal end is vibrated.

As noted above, in some embodiments, the tasks of anchoring the device and of applying repetitive motion is divided among the arms, with a possible overlap. The arms may thus vary in their shape, dimension, construction and/or composition, depending on the functionality of each arm. Moreover, one or more of the arms can be used for discharging a therapeutic substance and/or for applying electrical stimulation, as will be described below. These tasks may also impact the shape, dimension, construction and/or composition of the arm.

As noted above, the resonant frequency may vary from one arm to another. In some embodiments, each arm may comprise a feedback piezoelectric element. Using the feedback provided by these elements, controller 36 drives each arm at a different frequency that matches its individual resonant frequency. For example, controller 36 may comprise a feedback mechanism, which senses the vibration frequency of the feedback element of each arm and adjusts the frequency of the AC voltage driving this arm, attempting to maximize the vibration magnitude.

In some embodiments, each arm can be vibrated individually by controller 36. Alternatively, the arms can be divided into two or more subsets, with each subset actuated separately by the controller. For example, the controller can vibrate individual arms or subsets of arms in an alternating pattern, in order to reduce the energy consumption of the capsule. In some cases, the appetite-suppressing effect of the vibration can be enhanced by alternately vibrating different points on the inner stomach surface.

Figure 8A:
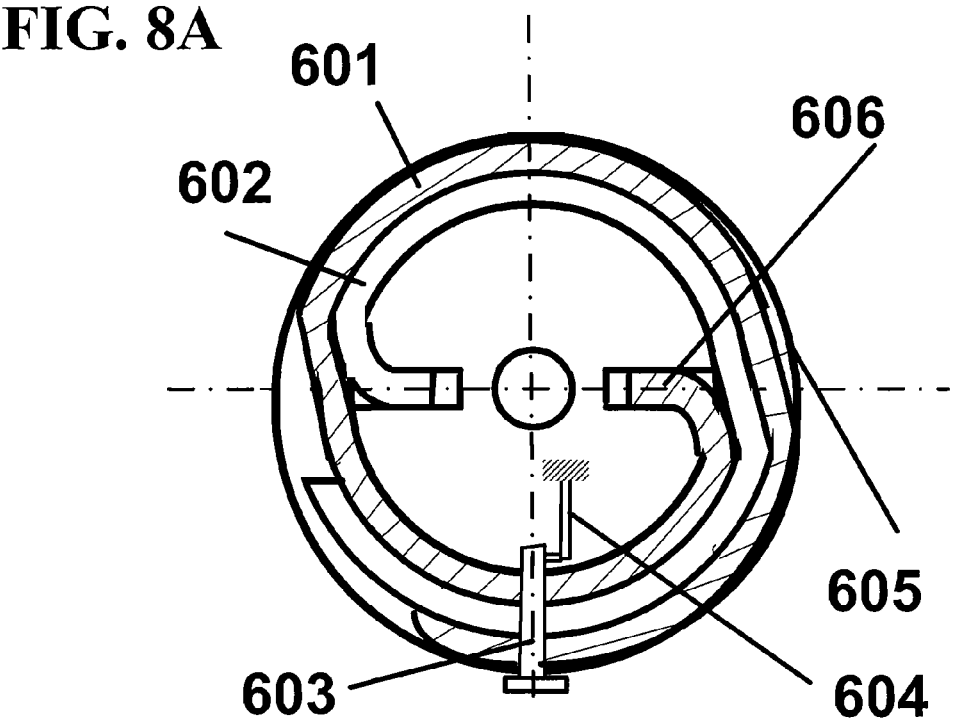
FIGS. 8A and 8B are transverse cross-sections of intrabody capsules, in accordance with embodiments of the present invention.

FIG. 8A is a transverse cross-section of an intrabody capsule, in accordance with an embodiment of the present invention. The transverse cross-section of FIG. 8A corresponds to the configuration of FIG. 4A above. The figure shows two flexible arms 601 (shaded) and 602 wrapped around the capsule body within a body contour 605. The arms are connected to the capsule body at arm bases 606. A lock/release mechanism comprises a pin 603 that is pushed out by a spring (not shown) and a shape memory alloy (SMA) beam or tension wire 604. When beam (or wire) 604 is actuated by the controller, pin 603 is released and separates from the capsule. As a result, arms 601 and 602 are free to self-extend. Alternatively, any other suitable actuation device can be used instead of SMA beam 604, such as, for example, a solenoid, a motor or a piezoelectric device. In alternative embodiments, a larger number of arms and/or longer arms that are wrapped several times over the perimeter of the capsule body can be used. The arms may be of different lengths.

In some embodiments, cover 605 may comprise a material that naturally dissolves in the stomach, such as Gelatin. In these embodiments, the dissolvable cover serves as a lock/release mechanism instead of the pin-based mechanism shown in the figure. When the capsule reaches the stomach, the cover dissolves and the arms are allowed to extend. Dissolvable covers made of Gelatin and other suitable materials are widely used in the pharmaceutical industry for controlled administration of substances in the stomach. Similar covers and materials can be used as dissolvable covers for the intrabody capsules described herein.

In some cases, the cover can be actively triggered to dissolve by having the patient drink a quantity of warm liquid, such as warm water. By using this technique, the caregiver can determine the specific location in the stomach in which to anchor the capsule. The cover can also be triggered or expedited by administering a chemical substance or drug, either by swallowing or by other routes of delivery.

Figure 8B:
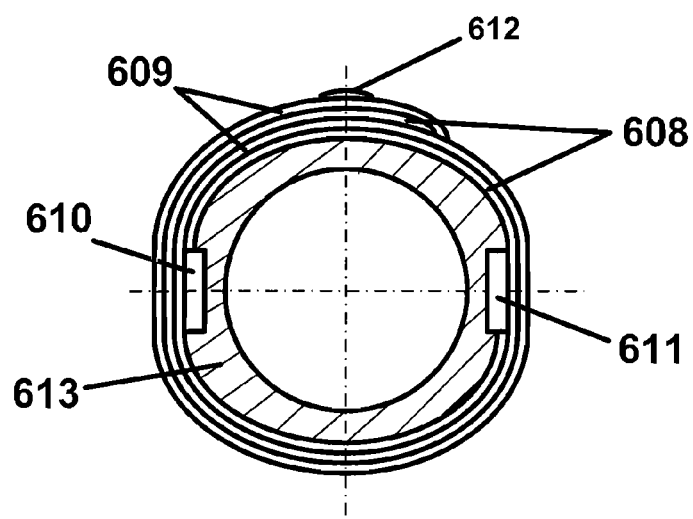

FIG. 8B is a transverse cross-section of an intrabody capsule, in accordance with another embodiment of the present invention. The transverse cross-section of FIG. 8B corresponds to the configuration of FIG. 4B above. The figure shows two flexible arms 608 and 609 wrapped around the capsule body and held in place by the upper part of a locking element 612. The locking element is shown in greater detail in FIG. 9B below. Although FIG. 8B shows two arms, any number of arms can be used.

Arm 608 comprises a thickened base 610, which is held in place after the extension of the arms. When released, the base disengages the entire arm from the capsule body. Similarly, arm 609 comprises a thickened base 611. The arms need not necessarily be of the same length. In the exemplary embodiment of FIG. 8B, a single locking element 612 is used to hold all arms. Alternatively, two or more locking elements may be used.

FIG. 9A is a cross-section of a lock and release mechanism of a self-extracting arm, in accordance with an embodiment of the present invention. The figure shows a pivot 703, around which an arm 702 rotates with respect to capsule body parts 705 and 706. Only parts of arm 702 and body 705 that are in close proximity to the pivot are shown. This mechanism can be used, for example, as pivot 103 in the capsule of FIG. 3A above.

Pivot 703 compresses a spring 701 and is held by a latch 704. When latch 704 is actuated (i.e., moved aside) by the controller, spring 701 pushes pivot 703 out of the capsule body. As a result, arm 702 is no longer held by pivot 703 and is now separated from capsule body 705. The latch can be actuated using any of the actuation methods described above.

FIG. 9B is a cross-section of a lock and release mechanism of a self-extending arm, in accordance with another embodiment of the present invention. The upper part of a central pin 713 holds folded arms 715 and 717 in the folded position against a capsule body 716. Pin 713 is locked in place by a detent 714. When the detent releases the pin after being triggered by the controller, a spring 711 pushes the pin outwards and releases the arms. The detent may comprise shape memory alloy (SMA), which bends or changes its shape by electric heating, a solenoid, a piezo-element or be moved by a motor.

FIG. 10 is a longitudinal cross section of an intrabody capsule, in accordance with an embodiment of the present invention. In the present example, the capsule comprises a reservoir 801, which is filled with a substance to be locally administered by the capsule. An electric valve 802, which is controlled by the controller, starts and stops the flow of substance out of the reservoir. One or more thin, flexible tubes 803 transfer the substance to the distal ends of arms 804, so as to discharge the substance adjacently to the tissue. The tubes are typically embedded in the arms. In alternative embodiments, the substance can be discharged from the reservoir in the general vicinity of the capsule, without the use of tubes.

The valve may be opened periodically by the controller in accordance with a pre-programmed profile. Alternatively, the valve can be opened on demand, by transmitting a suitable command from the external console. In alternative embodiments, the flow of substance from reservoir 801 can be regulated by any other suitable element, such as a pressure valve, a piezoelectric valve and a motor-operated pump. In some embodiments, the reservoir is pre-pressurized so that the substance flows freely when valve 802 is opened. Alternatively, the substance can be discharged using natural diffusion or using a chemical or capillary effect.

As noted above, substances can alternatively be discharged locally by impregnating the outer surface of the capsule body and/or arms with substance. As an example, the arms can be impregnated by Hexacapron and the substance released in the vicinity of bleeding tissue. As another example, the arms may be impregnated by Urokinase in order to treat blood clot.

Additionally or alternatively, the arms can be impregnated by any other suitable medication or chemical to induce and promote desired reactions in the target organ.

FIGS. 11A and 11B respectively show a longitudinal cross section and a transverse cross section of an intrabody capsule 902, in accordance with another embodiment of the present invention. Several intrabody capsule products are known in the art. Some known capsules are fitted with video cameras or other sensors and devices. In some embodiments, a known capsule can be modified to include self-unfolding arms, in accordance with the embodiments described herein. A desirable mode of operation for camera capsules is the possibility to anchor the capsule in a certain location in the gastrointestinal tract, and to move it slightly forwards and backwards around a location of interest.

The location of interest may be selected by a caregiver based on transmitted images or automatically by the capsule using suitable pattern recognition software. Based on the indications of the pattern recognition software, the capsule may also transmit alerts to console 14.

In FIG. 11A, capsule 902 comprises arms 904 and 906, which are shown in their tightly-packed position. Unlike some of the embodiments described above, in the present example the arms are held, expanded and contracted using a piezoelectric or electro-active effect. The arms may comprise any of the EAP, DEA or piezoelectric materials described above. As such, capsule 902 does not comprise a locking mechanism. In FIG. 11A arms 906 are shown parallel to the capsule body, while arms 904 are tilted at a certain angle with respect to the capsule body. In alternative embodiments, arms 906 can be tilted in the opposite direction or at any desired angle.

In FIG. 11B the arms (denoted 908) are shown in their expanded position. The capsule controller applies a suitable voltage to the EAP, DEA or piezoelectric material of the arms. As a result, the arms expand until they push against an outer tissue 914. The controller can cause the arms to contract by removing the voltage or by applying a different voltage to the arms. The controller may control each arm separately, or it may alternatively control groups of arms or all arms simultaneously.

Depending on the application, the tissue may comprise any element of the gastro-intestinal tract such as the colon, the small intestine or any hollow organ or tubular viscus within the body. The configuration of FIGS. 11A and 11B is particularly suitable for scenarios in which a modest deflection of the arms is sufficient to ensure anchoring, as shown in FIG. 11B. Such an application may comprise, for example, anchoring the capsule in the small intestine, whose diameter is only slightly larger than the diameter of the capsule or in a narrowed or blocked blood vessel. However, devices similar to device 902 may also be used in larger diameter organs such as the colon or stomach.

Figure 12A:
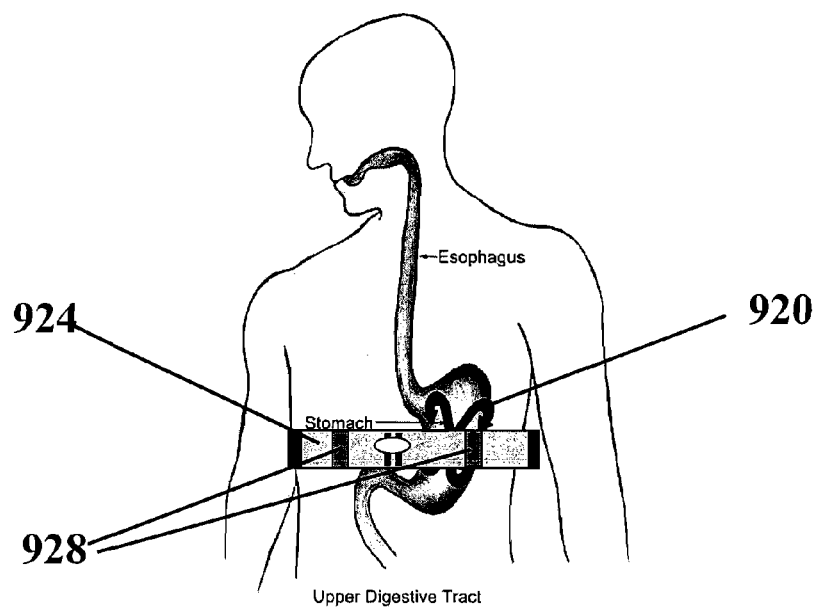
FIGS. 12A and 12B are schematic, pictorial illustrations of a system for treating obesity, in accordance with another embodiment of the present invention.
Figure 12B:
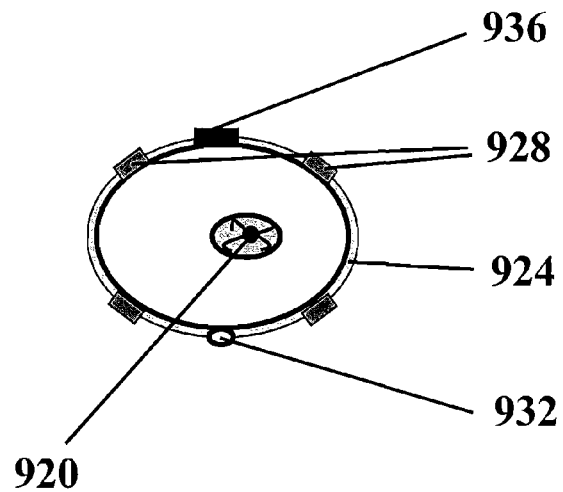

FIGS. 12A and 12B are schematic, pictorial illustrations of a system for treating obesity, in accordance with another embodiment of the present invention. FIG. 12A shows a front view of the system operating on a patient. FIG. 12B is an abdominal cross section, showing a top view of the system.

In the system of FIGS. 12A and 12B, a capsule 920 is inserted into the patient stomach. Capsule 920 comprises a field-responsive element, i.e., an element that can be attracted, deflected or otherwise displaced using magnetic induction. For example, the field-responsive element may comprise an element made of iron, a natural magnet, an electromagnet, or any other suitable material. In some cases, all or part of the capsule body may be constructed using such a material and serve as the field-responsive element.

The patient wears a belt 924, to which one or more electromagnets 928 are attached. The electromagnets generally surround capsule 920 and are able to apply magnetic fields in the vicinity of the capsule from several directions. The belt is typically fastened, tightened and held in place by a suitable fastening device 932.

A controller 936 applies electrical voltages to electromagnets 928, thus controlling the magnetic fields produced by the electromagnets. By applying a suitable pattern of electrical voltages, the controller can cause the set of electromagnets to produce a time-varying magnetic field in the vicinity of the capsule. The field-responsive element in the capsule moves, and causes the capsule body to move, in accordance with the magnetic field.

For example, the controller can actuate the electromagnets surrounding the patient in alternation, so that each electromagnet generates a pulsed electromagnetic field in its turn. As a result, the capsule body vibrates, and the arms apply repetitive motion to the inner stomach surface. The pattern, frequency, intensity and other characteristics of the repetitive motion of the arms are dependent upon the corresponding characteristics of the voltages generated by controller 936. The controller can be pre-programmed or otherwise controlled to apply any desired pattern or treatment profile.

In alternative embodiments of the present invention, the device is inserted into the stomach using laparoscopic surgery, surgical laparotomy, using an endoscope or similar procedure. Devices inserted in this manner can be made larger and may differ in configuration from swallowable capsules, since they do not need to fit in the patient's esophagus when collapsed. Larger capsules can be designed to apply more effective tissue stimulation, such as by using more arms and/or a higher complexity or higher intensity motion mechanism in comparison with swallowable capsules. In some embodiments, these capsules may comprise a remotely-charged power source, as described above, so as to extend the operational lifetime of the capsule. Typically, such capsules disassemble and evacuate from the body using any of the methods described above.

In some embodiments, the intrabody capsules described hereinabove can apply electrical stimulation to the inner surface of the stomach. The electrical stimulation can be combined with the stimulation caused by the motion of the arms and/or with local or systemic drug administration. The combined physical, electrical and/or chemical stimulation can enhance the appetite-suppression effects described above. For example, the capsule arms can be made of un-coated, electrically conductive material. Alternatively, the arms can be made of any desired material and coated with an electrically-conductive layer. The capsule power source can apply a suitable electrical signal to the contact points on the stomach surface via the electrically-conductive arms. The parameters of electrical stimulation, e.g., activation schedule, signal magnitude and coordination with physical stimulation and/or drug administration can be controlled using external commands and/or using a predefined treatment profile.

In some cases, the operation of the intrabody capsule can also be combined with a systemic administration of a drug or other substance. As described above, the local tissue stimulation carried out by the capsule induces systemic effects, such as (but not limited to) effects on the central nervous system. Thus, the combination of a systemically-administered substance and the tissue stimulation of the capsule can enhance these systemic effects beyond the separate contributions of the capsule or of the substance, i.e., provide a synergistic enhancement of the effects of each other.

Since the capsule induces systemic effects, which are not restricted to the specific location of the capsule in the body, the capsule enhances the activity of the substance indirectly. Similarly, the systemically-administered substance may enhance the effect of the capsule, either locally or systemically. For example, administration of a weight-loss drug having central effects, such as Rimonabant or Sibutramine, or any other substance having weight-loss or oral intake reduction properties, combined with capsule activation, will produce an enhanced, synergistic effect.

In some embodiments, the capsule may alert the patient to consume the substance at the appropriate time, e.g., in order to synchronize with the treatment profile carried out by the capsule. For example, in embodiments in which the capsule comprises a transmitter that transmits data from the capsule, the controller can transmit an alert message to the patient's personal control unit, indicating the appropriate time for consuming the substance.

The physical tissue stimulation by intrabody capsules can also be useful in promoting insulin secretion, such as in patients having altered glucose metabolism. It is well-known that insulin secretion depends on three stimuli—glucose, incretins and autonomic innervations. Physical intra-gastric stimulation by a suitable capsule will have a positive effect on two of these components, namely autonomic innervation and secretion of incretins.

Although the embodiments described herein mainly address a capsule, which is anchored in the gastrointestinal tract and produces tissue stimulation for reducing caloric intake, the principles of the present invention can also be used for additional applications. For example, similar capsules can be inserted into other luminal organs or systems, such as into a blood vessel or into the urinary tract. The dimensions of the capsule and arms should be adjusted to fit the organ of interest. As another example, a capsule can be inserted surgically through a narrow orifice and positioned within or adjacent to the tissue of interest.

Devices can be inserted, either invasively or non-invasively, into any suitable target organ, such as but not limited to the central nervous system, intra-abdominal organs, thoracic organs and limbs. In such cases, the device may be capsule-shaped or have any other shape suitable for use in the specific target organ.

In addition to reducing caloric intake, applying mechanical localized tissue stimulation can be used to treat other gastrointestinal conditions such as localized bleeding or inflammation. Localized substance delivery can also be used to reach specifically high concentrations of the substance while preventing systemic effects.

In some embodiments, certain medical conditions can be identified by examining the arms after they are disposed of by the patient body. For example, tissue residues deposited on the arms can be examined. The arms can be examined for the occurrence of certain chemical reactions, such as contact with blood and/or a change in PH value.

Additionally or alternatively, certain medical conditions, such as internal bleeding, can be sensed by the arms when the capsule is anchored in the target organ. The capsule can transmit to the external receiver indications of such conditions.

In some embodiments, controlling the motion of the extended arms can also be used to navigate the capsule inside the body, such as along the gastrointestinal tract. Navigation can either be autonomic or controlled by the external console. By regulating the extension of each arm separately, a movement along the capsule axis can be achieved.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A medical device, comprising:
a swallowable intra-body capsule including:
a capsule housing which is automatically dissolvable within the stomach of a patient;
at least one arm, located within the dissolvable capsule housing, which is configured to automatically extend outwardly within the stomach of a patient so as to contact at least one point-of-contact on an inner surface of the stomach;
a resonator located within said capsule housing and being operative to cause said at least one arm to apply a repetitive motion at said at least one point-of-contact; and
a controller, located within said capsule housing, which is arranged to automatically control application of said repetitive motion.

2. The device according to claim 1, wherein the repetitive motion comprises at least one motion type selected from a group of types consisting of a sliding motion, a tilting motion and a perpendicular pressure motion.

3. The device according to claim 1, wherein, when extended, the at least one arm is arranged to apply at least one stimulation type selected from a group of types consisting of a mechanical, a vibratory, a tactile and a nociceptive stimulation at said at least one point-of-contact.

4. The device according to claim 1, wherein the capsule is adapted to be inserted into one of a gastrointestinal tract of the patient, a blood vessel, a genito-urinary tract of the patient, part of a central nervous system, an intra-abdominal organ, a thoracic organ and a limb of the patient.

5. The device according to claim 1, wherein the device is adapted to be inserted into the stomach using at least one procedure selected from a group of procedures consisting of an invasive procedure, an endoscopic procedure, a laparoscopic surgery procedure and a surgical laparotomy procedure.

6. The device according to claim 1, wherein the at least one arm comprises at least one of a metal, a plastic, an electrically-actuated material, an ionic Electro-Active Polymer (EAP), an electronic EAP, a Dielectric Elastomer Actuator (DAE) and a piezoelectric material.

7. The device according to claim 1, wherein:
the at least one arm has a distal end; and
the repetitive motion measured at the distal end has a frequency between 0.1 Hz and 50 Hz and an amplitude of between 10 microns and 100 mm.

8. The device according to claim 1, and comprising an antenna and a receiver, which are arranged to receive external commands transmitted to the device from an external transmitter, and wherein said controller is operative to control an operation of the device responsively to the external commands.

9. The device according to claim 8, wherein the controller is arranged to cause the at least one arm extend responsively to the external commands.

10. The device according to claim 8, wherein the controller is arranged to cause the at least one arm disengage from the capsule responsively to the external commands.

11. The device according to claim 1, wherein the at least one arm has a base and includes at least one releasable attachment mechanism for attaching the base to the capsule when the at least one arm is extended, the attachment mechanism selected from a group of mechanisms consisting of a friction mechanism, a pin mechanism and a taper mechanism.

12. The device according to claim 1, and comprising a release mechanism, which is arranged to restrain the at least one arm during the insertion into the stomach, and wherein said controller is operative to actuate the release mechanism to release the at least one arm, so as to permit extension of the at least one within the stomach.

13. The device according to claim 12, wherein the at least one arm is elastic and arranged to assume an extended position when not restrained, and is wrapped around the capsule during the insertion into the stomach.

14. The device according to claim 12, wherein the at least one arm is wrapped around the capsule in multiple layers.

15. The device according to claim 12, wherein the at least one arm includes at least one material selected from a group of materials consisting of a piezoelectric material, a Dielectric Elastomer Actuator (DEA), an ionic Electro-Active Polymer (EAP) and an electronic EAP and wherein the controller is arranged to apply a voltage to the material so as to cause the at least one arm to extend.

16. The device according to claim 12, wherein the controller is arranged to determine a release condition and to actuate the release mechanism responsively to the release condition so as to cause the release mechanism to release the at least one arm.

17. The device according to claim 16, wherein the release condition comprises at least one of a predetermined time schedule, an event schedule and an external command transmitted to the device.

18. The device according to claim 16, wherein the release mechanism comprises at least one actuation device selected from a group of mechanisms consisting of a shape memory alloy (SMA) element, a motor, a piezoelectric element, an Electro-Active Polymer (EAP) element, a Dielectric Elastomer Actuator (DEA), a solenoid, a magnetic lock and a detent, and wherein the controller is arranged to actuate the release mechanism using the actuation device.

19. The device according to claim 1, and wherein said capsule housing is arranged to restrain the at least one arm during the insertion into the stomach and to dissolve in the stomach so as to release the at least one arm and permit the at least one arm to extend.

20. The device according to claim 19, wherein dissolution of the capsule housing is actuated by consumption of a substance by the patient.

21. The device according to claim 1, and comprising a disassembly mechanism, which is arranged, when activated, to disengage the at least one arm from the capsule so as to allow the capsule and the at least one arm to be disposed of.

22. The device according to claim 21, wherein the disassembly mechanism performs at least one action selected from a group of actions consisting of:
    releasing a circumferential ring that holds a first side of a base of the at least one arm;
    moving outward parts that are adjacent to a second side of the base of the at least one arm opposite the first side;
    removing pivots connecting the at least one to the capsule;
    releasing a friction mechanism; and
    pushing the base of the at least one arm out of a tapered locking mechanism.

23. The device according to claim 21, wherein the disassembly mechanism comprises one or more pre-energized springs that are released when the disassembly mechanism is activated.

24. The device according to claim 21, and wherein said controller is operative to actuate the disassembly mechanism responsively to a disassembly condition.

25. The device according to claim 24, wherein the disassembly condition comprises at least one condition selected from a group of conditions consisting of a predetermined time schedule, a low power condition of a power source of the device and an external command transmitted to the device.

26. The device according to claim 24, wherein the disassembly mechanism comprises at least one actuation element selected from a group of elements consisting of a shape memory alloy (SMA) element, a motor, a piezoelectric element, an Electro-Active Polymer (EAP) element, a solenoid, a ball lock mechanism, a magnetic lock and a detent, and wherein the controller is arranged to actuate the disassembly mechanism using the actuation element.

27. The device according to claim 1, wherein the resonator comprises at least one element selected from a group of elements consisting of a disk-shaped resonator, a bending resonator, a twist resonator, an electric motor that rotates an eccentric mass, a stepping motor, a piezoelectric exciter, an Electro-Active Polymer (EAP) resonator, an electrostrictive exciter and an electrostatic source.

28. The device according to claim 1, wherein the resonator is arranged to vibrate the at least one arm with a random vibration having a frequency within a bandwidth containing a resonant frequency of the at least one arm.

29. The device according to claim 1, wherein the at least one arm includes at least one material selected from a group of materials consisting of an electrically-actuated material, a piezoelectric material, a Dielectric Elastomer Actuator (DEA), an ionic Electro-Active Polymer (EAP) and an electronic EAP, and wherein said controller is operative to drive the at least one arm with an electrical signal so as to cause the at least one arm to apply the repetitive motion.

30. The device according to claim 29, wherein the electrical signal has a frequency that approximates a resonant frequency of the at least one arm, so as to cause the at least one arm to vibrate at the resonant frequency.

31. The device according to claim 29, wherein the at least one arm includes a feedback element, which is arranged to sense vibration of the at least one arm, and wherein the controller is arranged to adjust the frequency of the vibration of the at least one arm to match the resonant frequency of the at least one arm based on the vibration sensed by the feedback element.

32. The device according to claim 29, wherein the at least one arm includes at least two arms are partitioned into two or more subsets, and wherein the controller is arranged to drive the two or more subsets in alternation.

33. The device according to claim 1, wherein the at least one arm is further arranged to transfer an electrical stimulation to the at least one point-of-contact.

34. The device according to claim 1, wherein the device is arranged to discharge a substance within the stomach.

35. The device according to claim 34, wherein the substance is impregnated in at least one of an outer surface of the capsule and the at least one arm.

36. The device according to claim 34, and comprising a container holding the substance fitted in capsule.

37. The device according to claim 36, wherein one or more of the at least one arm comprises tubes, which are arranged to lead the substance from the container to the inner surface of the stomach so as to discharge the substance in a vicinity of the point-of-contact.

38. The device according to claim 36, and comprising a substance discharge mechanism, which is arranged to discharge the substance using at least one effect selected from a group of effects consisting of a chemical reaction, a capillary effect, a pressure effect and a piezoelectric effect.

39. The device according to claim 34, and wherein said controller is operative to discharge the substance responsively to at least one of an external command transmitted to the device and a pre-programmed schedule.

40. The device according to claim 1, and comprising a transmitter, which is arranged to transmit a status of the device to an external receiver.

41. The device according to claim 40, wherein the transmitter is arranged to transmit an alert message indicating an appropriate time for externally administering a systemically-acting substance to the patient, in order to enhance a therapeutic effect induced by the repetitive motion and the substance.

42. The device according to claim 1, wherein at least one of the capsule and the at least one arm comprise a material that provides visualization when imaged by a medical imaging system.

43. The device according to claim 1, wherein the at least one arm has curved a-traumatic distal ends.

44. The device according to claim 1, wherein the at least one arm has a curved profile so as to increase a structural rigidity of the at least one arm.

45. The device according to claim 1, wherein the device comprises a power source comprising at least one of a battery, a rechargeable battery and a radio frequency (RF) coil arranged to accept externally-transmitted RF energy.

46. The device according to claim 1, and wherein said controller is pre-programmed with one or more activation profiles defining respective time schedules for activating functions of the device.

47. The device according to claim 46, wherein the functions comprise at least one function selected from a group of functions consisting of releasing the at least one arm, applying the repetitive motion, disengaging the at least one arm from the capsule, discharging a substance from the device, switching to another activation profile and transmitting a status of the device.

48. The device according to claim 46, wherein the functions comprise applying the repetitive motion by the at least one arm and discharging a substance from the device, and wherein the controller is arranged to synchronize a timing of applying the repetitive motion and of discharging the substance, so as to enhance a therapeutic effect induced by the repetitive motion and the substance.

49. The device according to claim 1, wherein said repetitive motion causes a therapeutic effect in the patient, the therapeutic effect comprising at least one effect selected from a group of effects consisting of a systemic physiological effect and a therapeutic effect distant from the stomach.

50. The device according to claim 1, wherein said repetitive motion causes a therapeutic effect in the patient, the therapeutic effect comprising an alteration of a caloric intake of the patient.

51. The device according to claim 1, wherein said repetitive motion causes a therapeutic effect in the patient, the therapeutic effect comprising an alteration of a metabolic profile of mucosa in a vicinity of the device.

52. The device according to claim 1, wherein the repetitive motion induces a secretion of at least one substance selected from a group of substances consisting of a hormone, a peptide, a cytokine and a molecule by the stomach, and said repetitive motion causes a therapeutic effect in the patient, the therapeutic effect comprising at least one effect selected from a group of effects consisting of an endocrine, an autocrine and a paracrine effect.

53. The device according to claim 1, wherein said repetitive motion causes a therapeutic effect in the patient, the therapeutic effect comprising at least one effect selected from a group of effects consisting of a systemic effect and a local neurally-mediated physiological systemic effect, which is induced via afferent and efferent nervous system fibers.

54. The device according to claim 1, wherein the repetitive motion causes a secretion of at least one substance selected from a group of substances consisting of a hormone, a peptide, a cytokine and a molecule from an organ other than the stomach.

55. The device according to claim 1, wherein the repetitive motion stimulates mechanically-activated tissue receptors at the at least one point-of-contact.

56. The device according to claim 1, wherein the repetitive motion alters a physical tissue property at the at least one point-of-contact.

57. The device according to claim 56, wherein the physical tissue property comprises at least one property selected from a group of properties consisting of a permeability, an excitability, a temperature and a consistency at the at least one point-of-contact.

58. The device according to claim 1, wherein the repetitive motion modifies an intra-luminal pressure at the at least one point-of-contact, so as to induce a counter-dilation reaction.

59. The device according to claim 1, wherein the repetitive motion affects a secretion of at least one of a pro-feeding (orexigenic) and an anti-feeding (anorexogenic) hormone in accordance with a treatment profile, so as to control a caloric intake of the patient.

60. A method for treating a patient, comprising:
inserting into a stomach of the patient a swallowable intra-body capsule comprising a capsule housing which is automatically dissolvable within the stomach of a patient and at least one arm, located within the capsule housing which is configured to automatically extend outwardly within the stomach of a patient so as to contact at least one point-of-contact on an inner surface of the stomach, a resonator located within the capsule housing and being operative to cause the at least one arm to apply a repetitive motion at the at least one point-of-contact, and a controller, located within the capsule housing which is arranged to automatically control application of the repetitive motion;
causing the at least one arm to extend outward from the capsule within the stomach so as to contact the at least one point-of-contact; and
applying a repetitive motion by the at least one arm the at least one point-of-contact, so as to cause a therapeutic effect in the patient.

61. The method according to claim 60, wherein said applying comprises applying at least one motion type selected from a group of types consisting of a sliding motion, a tilting motion and a perpendicular pressure motion.

62. The method according to claim 60, wherein said applying the repetitive motion comprises applying at least one stimulation type selected from a group of types consisting of a mechanical, a vibratory, a tactile and a nociceptive stimulation at the at least one point-of-contact.

63. The method according to claim 60, wherein the inserting comprises inserting via at least one of a gastrointestinal tract of the patient, a blood vessel, a genito-urinary tract of the patient, part of a central nervous system, an intra-abdominal organ, a thoracic organ and a limb of the patient.

64. The method according to claim 60, wherein said inserting comprises swallowing the capsule by the patient.

65. The method according to claim 60, wherein said inserting comprises inserting the device using at least one procedure selected from a group of procedures consisting of an invasive procedure, an endoscopic procedure, a laparoscopic surgery procedure and a surgical laparotomy procedure.

66. The method according to claim 60, wherein the at least one arm comprises at least one of a metal, a plastic, an electrically-actuated material, an ionic Electro-Active Polymer (EAP), an electronic EAP, a Dielectric Elastomer Actuator (DAE) and a piezoelectric material.

67. The method according to claim 60, wherein the at least one arm has a distal end, and wherein the repetitive motion measured at the distal end has a frequency between 0.1 Hz and 50 Hz and an amplitude of between 10 microns and 100 mm.

68. The method according to claim 60, and comprising receiving external commands transmitted to the capsule from an external transmitter, and controlling an operation of the capsule responsively to the external commands.

69. The method according to claim 68, wherein said controlling comprises causing the at least one arm to extend from the capsule responsively to the external commands.

70. The method according to claim 68, wherein said controlling comprises causing the at least one arm to disengage from the capsule responsively to the external commands.

71. The method according to claim 60, wherein said inserting the device comprises restraining the at least one arm during the insertion into the stomach, and wherein causing the at least one arm to extend comprises releasing the at least one arm so as to permit extension of the at least one arm within the stomach.

72. The method according to claim 71, wherein the at least one arm is elastic and arranged to assume an extended position when not restrained, and wherein said restraining the comprises wrapping the at least one arm around the capsule during the insertion into the stomach.

73. The method according to claim 72, wherein said wrapping comprises wrapping the at least one arm around the capsule in multiple layers.

74. The device according to claim 71, wherein the at least one arm comprises at least one material selected from a group of materials consisting of a piezoelectric material, a Dielectric Elastomer Actuator (DEA), an ionic Electro-Active Polymer (EAP) and an electronic EAP, and wherein said causing the at least one arm to extend comprises applying a voltage to the material.

75. The method according to claim 71, wherein said releasing comprises determining a release condition and releasing the at least one arm responsively to the release condition.

76. The method according to claim 75, wherein the release condition comprises at least one of a predetermined time schedule and an external command transmitted to the capsule.

77. The method according to claim 71, wherein said releasing comprises actuating at least one actuation device selected from a group of mechanisms consisting of a shape memory alloy (SMA) element, a motor, a piezoelectric element, an Electro-Active Polymer (EAP) element, a Dielectric Elastomer Actuator (DEA), a solenoid, a magnetic lock and a detent.

78. The method according to claim 60, wherein said inserting comprises restraining the at least one arm using the capsule housing, and wherein causing the at least one arm to extend comprises causing the capsule housing to dissolve in the stomach so as to release the at least one arm and permit the at least one arm to extend.

79. The method according to claim 78, wherein said causing the capsule housing to dissolve comprises consuming a substance by the patient.

80. The method according to claim 60, and comprising disengaging the at least one arm from the capsule so as to allow the capsule and the at least one arm to be disposed of.

81. The method according to claim 80, wherein said disengaging the at least one arm comprises performing at least one action selected from a group of actions consisting of:
    releasing a circumferential ring that holds a first side of a base of the at least one arm;
    moving outward parts that are adjacent to a second side of the base of the at least one arm opposite the first side;
    removing pivots connecting the at least one arm to the capsule;
    releasing a friction mechanism; and
    pushing the base of the at least one arm out of a tapered locking mechanism.

82. The method according to claim 80, wherein said disengaging the at least one arm comprises releasing one or more pre-energized springs.

83. The method according to claim 80, wherein said disengaging the at least one arm comprises disengaging the at least one arm responsively to a disassembly condition.

84. The method according to claim 83, wherein the disassembly condition comprises at least one condition selected from a group of conditions consisting of a predetermined time schedule, a low power condition of a power source of the capsule device and an external command transmitted to the capsule.

85. The method according to claim 80, wherein said disengaging the at least one arm comprises actuating at least one actuation element selected from a group of elements consisting of a shape memory alloy (SMA) element, a motor, a piezoelectric element, an Electro-Active Polymer (EAP) element, a solenoid, a ball lock mechanism, a magnetic lock and a detent.

86. The method according to claim 60, wherein said applying comprises vibrating the at least one arm using the resonator.

87. The method according to claim 86, wherein said vibrating the at least one arm comprises vibrating the at least one arm with a random vibration having a frequency within a bandwidth containing a resonant frequency of the at least one arm.

88. The method according to claim 60, wherein the resonator comprises at least one element selected from a group of elements consisting of a disk-shaped resonator, a bending resonator, a twist resonator, an electric motor that rotates an eccentric mass, a stepping motor, a piezoelectric exciter, an Electro-Active Polymer (EAP) resonator, an electrostrictive exciter and an electrostatic source.

89. The method according to claim 60, wherein the at least one arm comprises at least one material selected from a group of materials consisting of an electrically-actuated material, a piezoelectric material, a Dielectric Elastomer Actuator (DEA), an ionic Electro-Active Polymer (EAP) and an electronic EAP, and wherein said applying comprises driving the at least one arm with an electrical signal.

90. The method according to claim 89, wherein the electrical signal has a frequency that approximates a resonant frequency of the at least one arm, so as to cause the at least one arm vibrate at the resonant frequency.

91. The method according to claim 90, wherein said applying comprises sensing vibration of the at least one arm using a feedback element attached to the at least one arm, and adjusting a frequency of the vibration of the at least one arm to match the resonant frequency of the at least one arm based on the vibration sensed by the feedback element.

92. The method according to claim 89, wherein the at least one arm includes at least two arms partitioned into two or more subsets, and wherein said driving comprises driving the two or more subsets in alternation.

93. The method according to claim 60, and comprising transferring an electrical stimulation to the at least one point-of-contact using the at least one arm.

94. The method according to claim 60, and comprising discharging a substance from the capsule within the stomach in order to induce the therapeutic effect.

95. The method according to claim 94, wherein said discharging comprises impregnating the substance in at least one of an outer surface of the capsule and the at least one arm.

96. The method according to claim 94, wherein said discharging comprises discharging the substance from a container fitted in the capsule.

97. The method according to claim 96, wherein said discharging the substance from a container comprises leading the substance from the container to the inner surface of the stomach using tubes along one or more of the at least one arm, so as to discharge the substance in a vicinity of the at least one point-of-contact.

98. The method according to claim 94, wherein said discharging comprises releasing the substance using at least one effect selected from a group of effects consisting of a chemical reaction, a capillary effect, a pressure effect and a piezoelectric effect.

99. The method according to claim 94, wherein said discharging comprises discharging the substance responsively to at least one of an external command transmitted to the capsule and a pre-programmed schedule.

100. The method according to claim 60, and comprising transmitting a status of the capsule to an external receiver.

101. The method according to claim 100, wherein said transmitting comprises transmitting an alert message indicating an appropriate time for externally administering a substance to the patient, in order to enhance the therapeutic effect.

102. The method according to claim 60, and comprising imaging the capsule using a medical imaging system, wherein at least one of the capsule and the at least one arm comprise a material that provides visualization when imaged by the medical imaging system.

103. The method according to claim 60, and comprising activating functions of the capsule in accordance with one or more time schedules defined by respective activation profiles pre-programmed in the capsule.

104. The method according to claim 103, wherein said activating functions comprises performing at least one action selected from a group of actions consisting of releasing the at least one arm, applying the repetitive motion, disengaging the at least one arm from the capsule, discharging a substance from the capsule, switching to another activation profile and transmitting a status of the capsule device.

105. The method according to claim 103, wherein said activating functions comprises synchronizing a timing of applying the repetitive motion by the at least one arm and of discharging a substance from the capsule, so as to enhance the therapeutic effect.

106. The method according to claim 60, wherein the capsule includes a field-responsive element, and wherein said applying comprises setting the capsule in motion by inducing a time-varying magnetic field in the field-responsive element using one or more electromagnets located externally to the patient, such that characteristics of the repetitive motion applied by the at least one arm depends on the time-varying magnetic field.

107. The method according to claim 60, and comprising administering to the patient a systemically-administered substance that contributes to the therapeutic effect, so as to enhance the therapeutic effect by synergistically using the substance and the repetitive motion.

108. The method according to claim 107, wherein said administering and applying comprises synchronizing a timing of said administering and of said applying so as to enhance the therapeutic effect.

* * * * *